(12) United States Patent
Naar et al.

(10) Patent No.: US 8,557,746 B2
(45) Date of Patent: Oct. 15, 2013

(54) HIGH THROUGHPUT SCREENS FOR SMALL-MOLECULE INHIBITORS OF THE NUCLEAR RECEPTOR-LIKE PATHWAY REGULATING MULTIDRUG RESISTANCE IN FUNGI

(75) Inventors: Anders M. Naar, Arlington, MA (US); Gerhard Wagner, Chestnut Hill, MA (US); Joy Nishikawa, Cambridge, MA (US); Haribabu Arthanari, Brookline, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 625 days.

(21) Appl. No.: 12/751,517

(22) Filed: Mar. 31, 2010

(65) Prior Publication Data
US 2010/0273676 A1  Oct. 28, 2010

Related U.S. Application Data

(60) Provisional application No. 61/165,669, filed on Apr. 1, 2009.

(51) Int. Cl.
*C40B 30/04* (2006.01)
*C40B 30/10* (2006.01)

(52) U.S. Cl.
USPC ............... 506/9; 506/12; 436/172; 422/82.08

(58) Field of Classification Search
USPC ....................... 506/9, 12; 436/172; 422/82.08
See application file for complete search history.

(56) References Cited

PUBLICATIONS

Näär et al. (Genes and Development, 2009, 23(4):419-432).*
Roehrl et al. (Biochemistry, 2004, 43:16056-16066).*
Thakur et al. (Nature, 2008, 452:604-611).*
Thakur et al., Nature, 452:604-611 (2008). "A nuclear receptor-like pathway regulating multidrug resistance in fungi."

* cited by examiner

*Primary Examiner* — Christopher M Babic
*Assistant Examiner* — Jeremy C Flinders
(74) *Attorney, Agent, or Firm* — Nixon Peabody LLP

(57) ABSTRACT

The present invention relates to the identification of molecular mechanisms associated with multidrug resistance (MDR) in fungal infections. More specifically, fungi harbor a nuclear receptor-like pathway controlling MDR, which represents a novel therapeutic target for the treatment of MDR in pathogenic fungi such as *C. glabrata*.

4 Claims, 12 Drawing Sheets

KIX DOMAINS

```
ScGal11p  (7-88)    QDKDTLSNAERAKNVNGLLQVLMDINTLNGGSSDTADKIRTHAKNFEAALPAKSSSKKEYNDSMNEKVAVRNTYNTRKNAV
HsARC105  (9-77)    DWRS---TAFRQKLVSQIEDAMRKAG------VAHSKSSKDWESHVFLKAKTRDEYLSIVARLIIHFRDIHNKKSQAS
MmCBP     (590-671) GWHEHVTQDLRSHLVHKLVQAIFPTPDPAALKDRRMENLVAYAKKVEGDMYESANSRDEYYHLLAEKIYKIQKELEEKRRSR
``` arrows/labels: V21O, V27O, E53A, K63Q, Y66D, S69D, M70E, Y74D, V76D, M77E, R78L

FIG. 3A

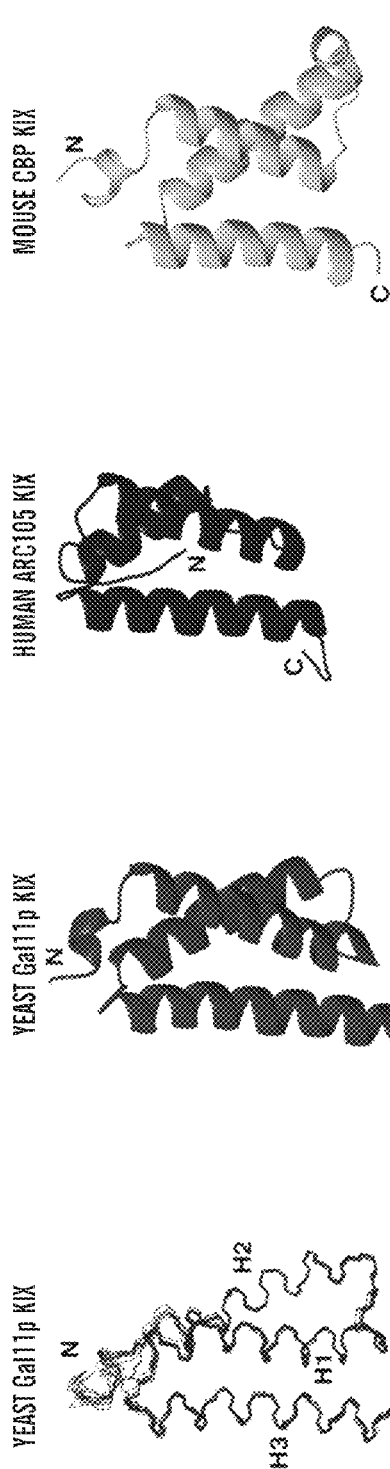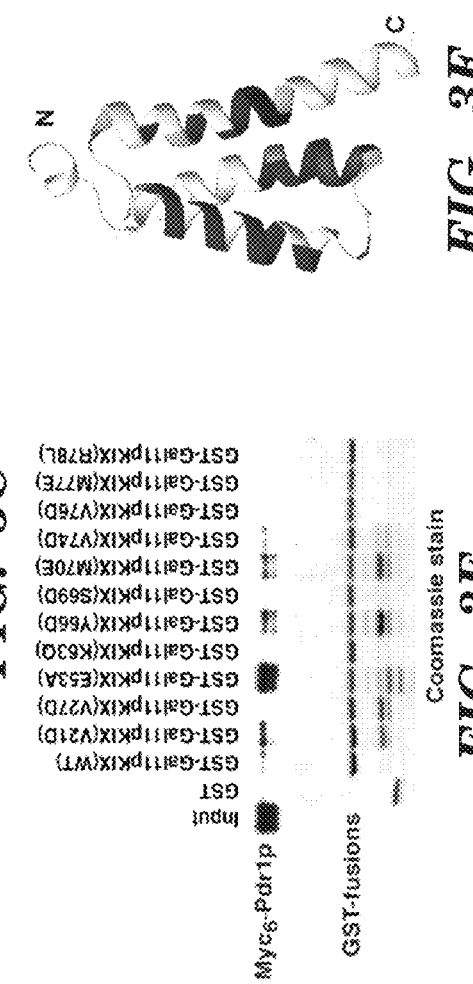

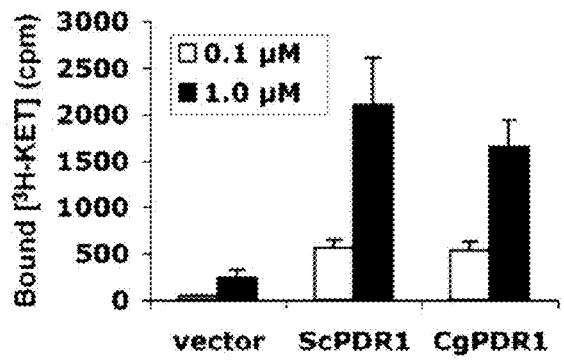
FIG. 4D
*C. glabrata* strains used and their interaction with *C. elegans*
| Strain | % Dead on Day 5 | % Dead on Day 6 | % Alive on Day 6 | P value (compared with corresponding WT condition) |
|---|---|---|---|---|
| CgBG2WT - Fluconazole | 26.52 | 23.86 | 6.06 | |
| Cgpdr1Δ - Fluconazole | 15.17 | 12.41 | 28.90 | $P < 0.0001$ |
| Cggal11AΔ - Fluconazole | 14.62 | 14.08 | 30.00 | $P < 0.0001$ |
FIG. 4E
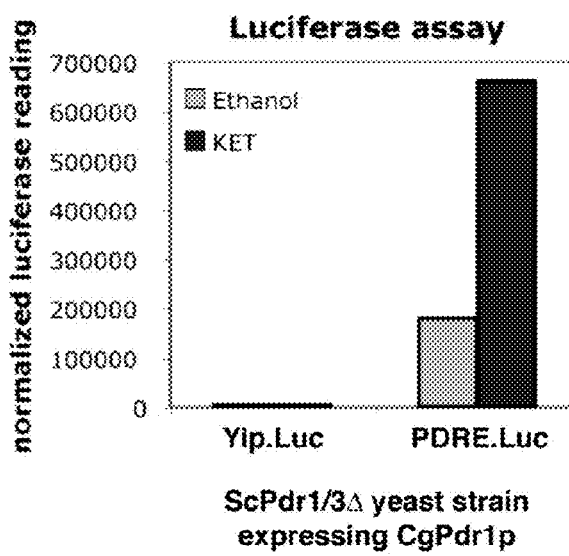
FIG. 5

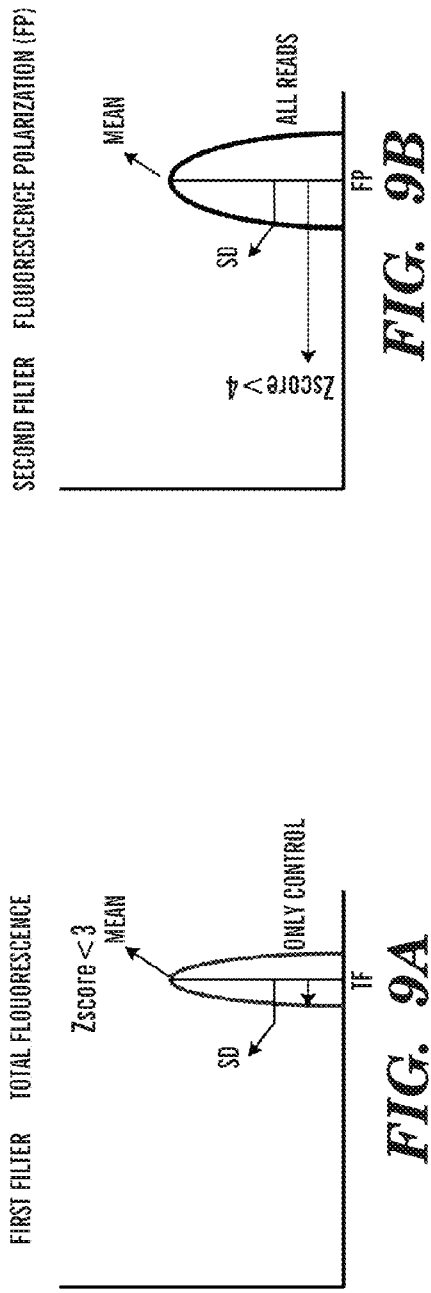
FIG. 9A
FIG. 9B
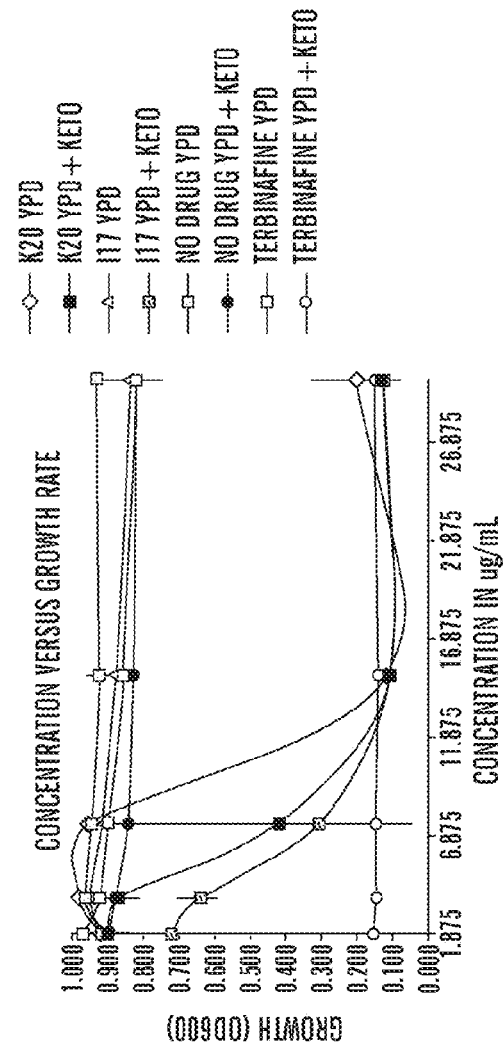
FIG. 10

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acttctggat tgtttggccg                                                   20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcaatgact ccctcacagt gg                                                22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aataactgct gacttggtgg cc                                                22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccaacatgaa gaccaagtgc tg                                                22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctccgtctgg attggtggtt ct                                                22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 6
cgcgcacaaa agcagagatt a                                                21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaggtgccaa acagaaaggt ga                                               22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggtcgcatt ggaggttata ga                                               22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctccaccact gctgaaagag                                                  20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtcaatacc agcagattct ag                                               22

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Asp Leu Tyr Ser Ile Leu Trp Ser Asp Val Tyr
1               5                   10

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 12

Glu Pro Cys Asp Leu Asp Ala Ala Leu Leu Thr Asp Ile Glu Asp Met
1               5                   10                  15

Leu Gln Leu Ile Asn Asn Gln Asp Ser Asp
            20                  25

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Tyr Asn Ser Leu Trp Gly Asp Leu Phe Ser Asp Val Tyr Leu
1               5                   10                  15

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Gly Thr Leu Asp Glu Phe Val Asn Lys Gly Asp Leu Asn Glu Leu
1               5                   10                  15

Tyr Asn Ser Leu Trp Gly Asp Leu Phe Ser Asp Val Tyr Leu
            20                  25                  30

<210> SEQ ID NO 15
<211> LENGTH: 82
<212> TYPE: PRT
<213> ORGANISM: Saccharomyces cerevisiae

<400> SEQUENCE: 15

Gln Asp Lys Asp Thr Leu Ser Asn Ala Glu Arg Ala Lys Asn Val Asn
1               5                   10                  15

Gly Leu Leu Gln Val Leu Met Asp Ile Asn Thr Leu Asn Gly Gly Ser
            20                  25                  30

Ser Asp Thr Ala Asp Lys Ile Arg Ile His Ala Lys Asn Phe Glu Ala
        35                  40                  45

Ala Leu Phe Ala Lys Ser Ser Lys Lys Glu Tyr Met Asp Ser Met
    50                  55                  60

Asn Glu Lys Val Ala Val Met Arg Asn Thr Tyr Asn Thr Arg Lys Asn
65                  70                  75                  80

Ala Val

<210> SEQ ID NO 16
<211> LENGTH: 69
<212> TYPE: PRT
<213> ORGANISM: Homo sapiens

<400> SEQUENCE: 16

Asp Trp Arg Ser Thr Ala Phe Arg Gln Lys Leu Val Ser Gln Ile Glu
1               5                   10                  15

Asp Ala Met Arg Lys Ala Gly Val Ala His Ser Lys Ser Ser Lys Asp
            20                  25                  30

Met Glu Ser His Val Phe Leu Lys Ala Lys Thr Arg Asp Glu Tyr Leu
        35                  40                  45
```

```
Ser Leu Val Ala Arg Leu Ile Ile His Phe Arg Asp Ile His Asn Lys
        50                  55                  60

Lys Ser Gln Ala Ser
 65

<210> SEQ ID NO 17
<211> LENGTH: 82
<212> TYPE: PRT
<213> ORGANISM: Mus musculus

<400> SEQUENCE: 17

Gly Trp His Glu His Val Thr Gln Asp Leu Arg Ser His Leu Val His
 1               5                  10                  15

Lys Leu Val Gln Ala Ile Phe Pro Thr Pro Asp Pro Ala Ala Leu Lys
            20                  25                  30

Asp Arg Arg Met Glu Asn Leu Val Ala Tyr Ala Lys Lys Val Glu Gly
        35                  40                  45

Asp Met Tyr Glu Ser Ala Asn Ser Arg Asp Glu Tyr Tyr His Leu Leu
    50                  55                  60

Ala Glu Lys Ile Tyr Lys Ile Gln Lys Glu Leu Glu Glu Lys Arg Arg
 65                 70                  75                  80

Ser Arg

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
 1               5
```

HIGH THROUGHPUT SCREENS FOR SMALL-MOLECULE INHIBITORS OF THE NUCLEAR RECEPTOR-LIKE PATHWAY REGULATING MULTIDRUG RESISTANCE IN FUNGI

CROSS REFERENCE TO RELATED APPLICATIONS

The present application claims the benefit of priority under 35 U.S.C. §119(e) of U.S. Provisional Application No. 61/165,669, filed Apr. 1, 2009, incorporated herein by reference.

FEDERAL FUNDING LEGEND

This invention was made with government support under grants No. GM071449, No. CA127990, No. A1046223, No. GM47467, No. GM49325 and No. GM30186, each awarded by the National Institutes of Health. The U.S. government has certain rights in the invention.

FIELD OF THE INVENTION

The present invention relates to the identification of molecular mechanisms associated with multidrug resistance (MDR) in fungal infections. More specifically, fungi harbor a nuclear receptor-like pathway controlling MDR, which represents a novel therapeutic target for the treatment of MDR in pathogenic fungi such as *C. glabrata*.

BACKGROUND

Multidrug resistance, a phenomenon defined as the ability of cells to acquire resistance to a wide range of structurally and functionally distinct cytotoxic or cytostatic compounds, is often caused by overexpression of drug efflux pumps resulting in the expulsion of a wide variety of molecules, and presents a major obstacle in the treatment of infectious disease caused by bacterial and fungal pathogens. MDR is a serious complication during treatment of opportunistic fungal infections that frequently afflict immunocompromised individuals, such as transplant recipients and cancer patients undergoing cytotoxic chemotherapy. Improved knowledge of the molecular pathways controlling MDR in pathogenic fungi should facilitate the development of novel therapies to combat these intransigent infections. MDR is often caused by up-regulation of transporters (e.g. P-glycoprotein) that facilitate extrusion of a wide range of toxic chemicals and drugs. The molecular mechanisms, however, are poorly understood.

Pathogenic fungi, especially *Candida* species, have emerged as important and prevalent opportunistic infections in individuals with compromised immunity, including those suffering from AIDS, cancer patients treated with chemotherapy, transplant recipients on immunosuppressive drugs, and patients with advanced diabetes. *Candida* species now account for 8% to 9% of all blood stream infections, with crude mortality rates of 40%. Significantly, both intrinsic and acquired MDR is an important complication of fungal infections. *C. glabrata*, which exhibits strong MDR, is emerging as a clinically important fungal pathogen, accounting, for example, for 20% to 24% of *Candida* blood stream infections in the U.S. There is thus an urgent need to elucidate the mechanisms underpinning MDR in pathogenic fungi to develop novel antifungal treatments.

SUMMARY

The present invention provides for a detailed mechanistic understanding of a fungal nuclear receptor-like gene regulatory pathway and provides novel therapeutic targets for the treatment of multidrug-resistant fungal infections. The invention identifies the mechanisms of how MDR is controlled in fungi in response to xenobiotics, and then uses this knowledge to identify novel therapeutic strategies to combat MDR in pathogenic fungi, such as *Candida* spp. More specifically, the present invention relates to Pdr1p family members in *Saccharomyces cerevisiae* and the human pathogen *C. glabrata* that bind directly to structurally diverse drugs and xenobiotics, resulting in stimulated expression of drug efflux pumps and induction of MDR. Notably, this is mechanistically similar to regulation of MDR in vertebrates by the PXR nuclear receptor, indicating an unexpected functional analogy of fungal and metazoan regulators of MDR. The present invention also relates to critical and specific roles of the Gal11p/MED15 subunit of the Mediator co-activator and its activator-targeted KIX domain in antifungal/xenobiotic-dependent regulation of MDR.

Thus, an embodiment of the present invention provides for a high-throughput screen for small-molecule antagonists of xenobiotic-dependent transactivation by *Candida glabrata* Pdr1p (CgPdr1p). This important methodology enables biomedical researchers to extend molecular imaging studies and use high throughput screening for drugs (e.g., agents or small molecules). For example, cells may be grown and tested in a 384-well format. Visualization and scoring may be completely mechanized.

Embodiments of the present invention provide for high throughput screening of xenobiotics that act in fungi by a direct-effector pathway, for example, small-molecule inhibitors of the *C. glabrata* Pdr1p orthologs that inhibit CgPdr1p activation domain (AD) binding to CgGal11Ap KIX. One embodiment is a high throughput fluorescence polarization assay comprising a fluorescein-tagged portion of *C. glabrata* Pdr1pAD and a recombinant Gal11Ap KIX, wherein a small molecule that inhibits binding between the fluorescein-tagged Pdr1p and the Gal11Ap KIX affects fluorescence polarization. In an aspect of the invention, the portion of the Pdr1pAD is derived from the C-terminal 10 to 40 amino acids of the AD. In a particular embodiment, the Pdr1p is a fluorescein-conjugated 30-amino acid CgPdr1pAD peptide. In another particular embodiment, the Gal11Ap KIX domain is GST-tagged CgGal11Ap KIX. The fluorescence polarization assay may be fully or partially automated.

In another embodiment, the high throughput screening is a luminescence assay. In particular aspects, the luminescence screen comprises a pdr1Δ pdr3Δ *S. cerevisiae* strain expressing *C. glabrata* Pdr1 or a wild type *C. glabrata* strain bearing the luciferase gene under the control of pleiotropic drug response element motifs (PDREs), which are used to examine the effects of small-molecule inhibitors in down-regulating PDRE-dependent transcription. In an aspect of this embodiment, a strain with luciferase under the control of oleic acid-response elements (ORE) is used as a control in parallel with the PDRE-dependent strains. After cells are grown in the presence of the test drug, D-luciferin is added and luminescence read. This assay may be automated in embodiments of the present invention.

DESCRIPTION OF THE DRAWINGS

FIG. 1 shows data demonstrating that Pdr1p is a xenobiotic receptor.

FIG. 2 demonstrates the requirement for the Gal11p Mediator subunit and its KIX domain in Pdr1p/Pdr3p-dependent transcription of target genes and MDR.

FIG. 3 depicts the sequence and structure of the yeast Gal11p KIX domain and structural/mutational analysis of the Pdr1pAD-Gal11p KIX interface. FIG. 3a, Sequence alignment shows the similarity (in bold) between the yeast (Sc) Gal11p KIX (SEQ ID NO: 15)domain and the KIX domains of human (Hs) ARC105/MED15 (SEQ ID NO: 16) and mouse (Mm) CBP (SEQ ID NO: 17) co-activators. Conserved hydrophobic amino acids are highlighted. Helices are indicated by gray boxes. The point-mutated amino acids in the Gal11p KIX domain are indicated by arrows, with mutations that affect binding with Pdr1p in bold. FIG. 3b, Representation showing the 10 lowest energy solution structures of the Gal11p KIX domain. FIG. 3c, Ribbon diagram of the mean solution structures of yeast Gal11p, human ARC105/MED15, and mouse CBP KIX domains. FIG. 3d, Surface representation of Gal11p KIX with the Pdr1pAD-12 interaction surface (molar ratio 5:1 Gal11p KIX:Pdr1pAD-12). The residues correspond to a chemical shift change of more than 0.02 ppm. FIG. 3e, Binding of Myc$_6$-Pdr1p to point-mutated GST-Gal11p KIX domain fusion proteins in a GST-pulldown assay. Top panel: Myc$_6$-Pdr1p binding as detected by anti-Myc immunoblotting. Bottom panel: GST-Gal11p KIX fusion proteins as detected by Coomassie staining. FIG. 3f, Ribbon representation of Gal11p KIX where the residues correspond to a chemical shift change of more than 0.02 ppm upon addition of Pdr1pAD-12 (molar ratio of 5:1 Gal11p KIX:Pdr1pAD-12). Residues whose mutation disrupt binding to Myc$_6$-Pdr1p represent the residues implicated in Pdr1p binding by both NMR and mutational studies.

FIG. 4 shows dissection of the molecular mechanism of drug resistance in *C. glabrata*. FIG. 4d, Binding of $^3$H-KET with CgPdr1p. Beads with immunopurified Myc$_6$-CgPdr1p or Myc$_6$-ScPdr1p were used for binding assays. Mean values from triplicate experiments are shown; error bars, s.d. FIG. 4e, Effect of fluconazole on killing of *C. elegans* by wild-type or mutant strains of *C. glabrata* on days 5 and 6 (120 hr and 144 hr). Fluconazole increased the lifespan of nematodes when the CgPDR1 and CgGAL11A genes were deleted in *C. glabrata*. p values were calculated based on the entire 6-day experiment, with log-rank and Wilcoxon tests performed by STATA 6 statistical software.

FIG. 5 shows development of a yeast luciferase reporter strain expressing CgPdr1p in place of ScPdr1p/Pdr3p that can mediate potent PDRE-dependent and xenobiotic-stimulated transactivation. YIP.Luc represents a strain harboring the luciferase reporter vector without PDREs, whereas PDRE.Luc represents a strain that harbors a vector with three canonical PDREs driving luciferase expression. The PDRE-containing vector mediates increased basal activity as well as ketoconazole-stimulated activity, as compared with the vector lacking PDREs.

FIG. 9 depicts a high throughput screening approach in which a first filter selects for compounds that have total fluorescence value that is less than three standard deviation from the control wells (wells that do not contain any compound) (FIG. 9a); then a second filter chooses those compounds that have a Z-score of greater than 4 in fluorescence polarization (FIG. 9b).

FIG. 10 is a chart showing the concentration-dependent growth inhibition of drug 117 only in the presence of ketoconazole; drug K20 shows concentration-dependent growth inhibition in both the presence and absence of ketoconazole.

DETAILED DESCRIPTION

Figure 1A:
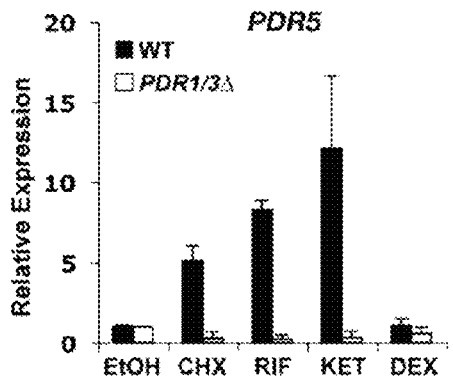
FIG. 1a, Xenobiotic-induced transcription of the PDR5 gene is dependent on Pdr1p/Pdr3p. QRT-PCR reactions were performed in triplicate. Mean values from three independent experiments are shown and error bars represent standard deviation.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention provides for orthologs of the fungal zinc cluster transcription factor Pdr1p in S. cerevisiae and the human pathogen C. glabrata that function in a manner similar to the mammalian nuclear receptor PXR. Both Pdr1p orthologs and PXR bind directly to structurally unrelated xenobiotics and drugs and, as a result, activate the expression of genes encoding ATP-dependent drug efflux pumps (e.g., P-glycoprotein/MDR1 orthologs). These xenobiotic-stimulated gene expression programs represent key contributors in both mammals and fungi to MDR, a phenomenon of increased resistance to chemically distinct drugs that impedes cancer chemotherapy and treatment of fungal infections, respectively.

MDR in fungi is caused by the overexpression of membrane-spanning efflux pumps (for example the ATP-binding cassette (ABC) family of transporters), resulting in the expulsion of various structurally unrelated molecules. Sipos & Kuchler, 7 Cum Drug Targets 471-81 (2006). Studies in S. cerevisiae have shown that the zinc-cluster transcription factor Pdr1p and the paralog Pdr3p together confer resistance to several drugs and toxins through transcriptional activation of ABC transporter genes and members of the major facilitator superfamily of drug efflux pumps, including Pdr5p, Snq2p and Yor1p, as well as phospholipid-transfer proteins such as Pdr16p. Balzi et al. 262 J. Biol. Chem. 16871-79 (1987); Meyers et al., 21 Curr. Genet. 431-36 (1992); Balzi et al., 269. J. Biol. Chem. 2206-14 (1994); Katzmann et al., 14 Mol. Cell. Biol. 4653-61 (1994); Delaveau et al., 244 Mol. Gen. Genet. 501-11 (1994); Decottignies et al., 270 J. Biol. Chem. 18150-57 (1995); Katzmann et al., 15 Mol. Cell. Biol. 15, 6875-83 (1995); van don Hazel et al., 274 J. Biol. Chem. 1934-41 (1999); Moye-Rowley, 73 Prog. Nucl. Acid Res. Mol. Biol. 251-79 (2003).

Several studies recently reported increased expression of drug efflux pumps in yeast in response to different xenobiotics, and demonstrated a requirement for Pdr1p/Pdr3p in this response, although the xenobiotic signaling pathway was not elucidated. Fylamnun et al., 559 FEBS Lett. 111-17 (2004); Gao et al., 279 J. Biol. Chem. 42677-86 (2004); Lucau-Danna et al., 25 Mol. Cell. Biol. 1860-68 (2005); Alenquer et al., 6 FEMS Yeast Res. 1130-39 (2006); Fardeau et al., 282 J. Biol. Chem. 5063-74 (2007). *C. glabrata* is evolutionarily closely related to *S. cerevisiae*, and recent studies have identified a Pdr1p ortholog (CgPdr1p) in *C. glabrata* that regulates drug efflux pumps and controls MDR in this pathogen. Vermitsky & Edlind, 38 Antimicrob. Agents Chemother. 3773-31 (2004); Tsai, 50 Antimicrob. Agents Chemother. 384-92 (2006); Vermitsky et al., 61 Mol. Microbial. 704-22 (2006). Increased knowledge of the mechanistic basis of CgPdr1p function in regulating multidrug resistance in *C. glabrata* could allow the identification of new classes of drugs to combat MDR in these clinically challenging infections.

Interestingly, the mammalian nuclear receptor pregnane X receptor (PXR) upregulates transcription of ABC transporters as well as cytochrome P450 detoxification enzymes in response to direct binding to structurally diverse xenobiotics. Kliewer et al., 23 Endocr. Rev. 687-702 (2002); Willson & Kliewer 1 Nature Rev. Drug Discov. 259-66 (2002). Similar direct transcription signaling mechanisms to regulate MDR have not yet been documented in non-vertebrate eukaryotes, however.

Transcription activators recruit co-activators that facilitate gene activation. Näär et al., 70 Ann. Rev. Biochem. 475-501 (2001). The Mediator co-activator, first characterized in yeast, interacts with RNA polymerase II and is involved in many transcriptional regulatory pathways. Kornberg, 30 Trends Biochem. Sci. 235-39 (2005). The co-activator requirements, including a possible role of Mediator, for xenobiotic-dependent transactivation of the MDR program by Pdr1p orthologs have not been determined. Identification of co-activator targets for Pdr1p orthologs could facilitate the development of novel anti-MDR agents that target the activator/co-activator interface.

The present invention shows that the Pdr1p orthologs in *S. cerevisiae* and *C. glabrata* bind directly to xenobiotics to activate genes encoding drug efflux pumps, and exhibit functional characteristics that are mechanistically similar to the vertebrate xenobiotic receptor PXR. Moreover, the results described herein demonstrate an essential and specific role for the Mediator co-activator subunit Gal11p (also known as MED15) in xenobiotic-dependent gene activation and MDR in *S. cerevisiae* and *C. glabrata*. The activation domains of Pdr1p orthologs bind directly to a domain present in Gal11p that is structurally conserved with the activator-binding KIX domain found in the human ARC105/MED15 Mediator subunit and in vertebrate CBP/p300 acetyltransferases. These results demonstrate that fungi harbor a nuclear receptor-like pathway controlling MDR, which represents a novel therapeutic target for the treatment of MDR in pathogenic fungi such as *C. glabrata*.

Pdr1p and Pdr3p are xenobiotic receptors. The expression of ATP-dependent drug efflux pumps (for example PDR5) and other Pdr1p/Pdr3p target genes (for example PDR16) in *S. cerevisiae* can be induced by chemically distinct drugs and xenobiotics, including the antifungal ketoconazole, the translation inhibitor cycloheximide and the classic PXR agonist rifampicin, in a Pdr1p/Pdr3p-dependent manner (FIG. 1a). In contrast, the glucocorticoid receptor agonist dexamethasone was consistently a poor inducer of Pdr1p/Pdr3p-regulated genes (FIG. 1a). Because the mammalian nuclear receptor PXR controls MDR gene expression by direct binding to xenobiotics (Kliewer et al., 2002; Willson & Kliewer, 2002), and based on the intriguing functional similarities of Pdr1p/Pdr3p to PXR, it was investigated whether Pdr1p and Pdr3p could also directly interact with xenobiotics to stimulate expression of their target genes.

Figure 1B:
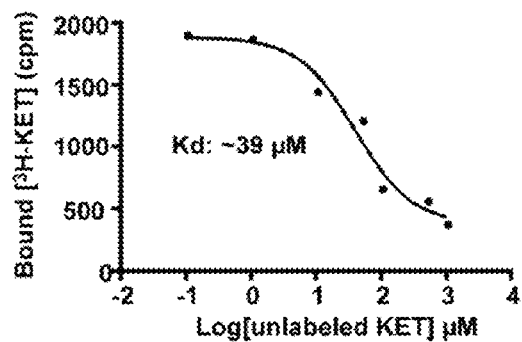
FIG. 1b, Pdr1p directly binds to the antifungal ketoconazole. Cold ligand competition was used to determine the binding affinity of $^3$H-KET to Myc$_6$-Pdr1p. 0.1 µM of $^3$H-KET was used for this experiment. Logarithmic concentration of unlabelled KET is displayed on the X-axis. Mean values from triplicate samples are shown. The graph was generated using GraphPad Prism4.
Figure 1C:
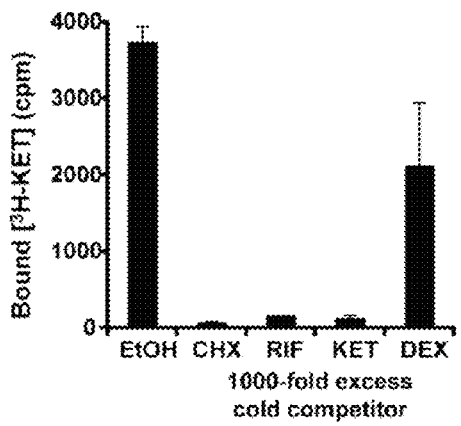
FIG. 1c, Cold competition assay reveals binding of various xenobiotics to Myc$_6$-Pdr1p. Unlabeled xenobiotics (EtOH, ethanol, vehicle; CHX, cycloheximide; RIF, rifampicin; KET, ketoconazole; DEX, dexamethasone) were used for competition (X-axis). The experiment was performed in triplicate. Mean values are shown and error bars represent standard deviation.

Importantly, immunopurified Pdr1p binds ketoconazole with a dissociation constant ($K_D$) of about 39 μM, similar to the range of binding affinities (mid-nanomolar to high micromolar) of ligands for mammalian PXR (FIG. 1b). Kliewer et al., 2002. Binding of radiolabelled ketoconazole to Pdr1p was effectively competed by unlabelled xenobiotics that activate Pdr1p/Pdr3p target genes in vivo, including rifampicin, cycloheximide, and ketoconazole itself (FIGS. 1b, 1c). Similar results were obtained with the Pdr1p paralog Pdr3p, consistent with its functional redundancy in gene expression assays with these xenobiotics (data not shown).

Figure 1D:
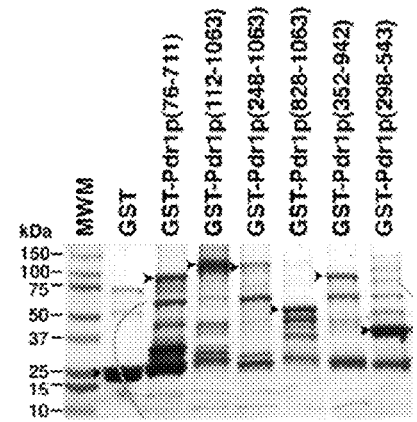
FIG. 1d, Expression of GST-Pdr1p proteins used in FIG. 1e as visualized by Coomassie stained gel. Arrows indicate full-length GST-fusion proteins.
Figure 1E:
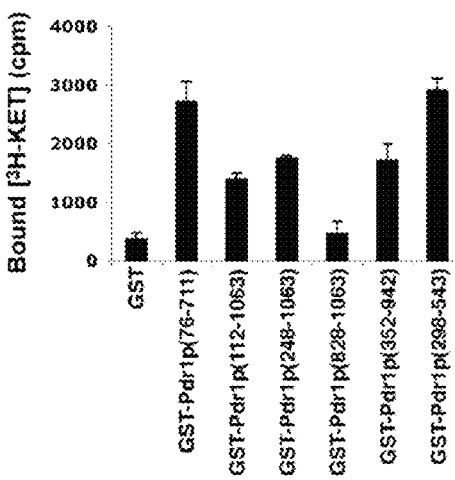
FIG. 1e, Binding of $^3$H-KET with various GST-Pdr1p fragments shows that the minimal region required for xenobiotic binding resides in a fragment of aa 352-543. Glutathione-sepharose beads with GST alone or different GST-Pdr1p proteins were used for direct binding with radiolabeled ketoconazole. Mean values from three independent replicates are shown, and error bars represent standard deviation.
Figure 1F:
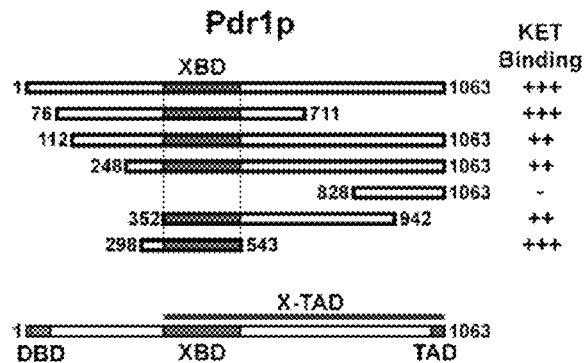
FIG. 1f, Schematic representation of the xenobiotic-binding domain of Pdr1p. Glutathione-sepharose beads with GST-Pdr1p protein fragments were used for direct binding assays using 0.1 µM of $^3$H-KET. '+' indicates binding whereas '−' indicates no binding. Lower cartoon shows positions of the DNA binding domain (DBD), the xenobiotic binding domain (XBD), and the xenobiotic-responsive transactivation domain (X-TAD). Color versions of some figures may be found at Thakur et al., 452 Nature 604-09 (2008).

Deletion analysis revealed that a small region in Pdr1p (amino acids 352-543) carboxy (C)-terminal to the DNA-binding domain is sufficient for binding to ketoconazole (FIG. 1d-f). A similar region in Pdr3p also mediates ketoconazole binding, supporting the notion of a discrete xenobiotic-binding domain (XBD) in this family of zinc-cluster transcription factors (data not shown). Nuclear receptors harbor autonomous ligand-binding domains and ligand-responsive activation domains located C-terminal to the zinc finger DNA-binding domain that can be transferred to heterologous DNA-binding domains. Fusion experiments to the yeast Gal4p DNA-binding domain (Gal4pDBD) identified a large C-terminal domain in Pdr1p (amino acids 352-1063), encompassing both the XBD and the C-terminal activation domain, as the minimal transferable xenobiotic-responsive transactivation domain (X-TAD; FIG. 1f and data not shown). These results demonstrate that yeast Pdr1p/Pdr3p activate transcription of target genes in response to direct binding to specific xenobiotics by a discrete transferable ligand-binding domain, suggesting that these critical transcription regulators of MDR in yeast function in a manner analogous to the vertebrate nuclear receptor PXR.

Figure 2A:
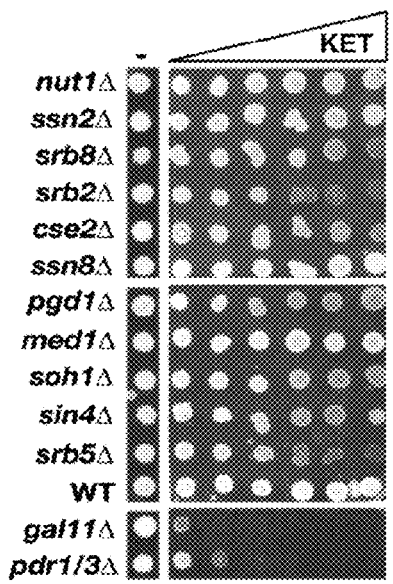
FIG. 2a shows growth of yeast cells on 1% yeast extract, 2% peptone and 2% dextrose (YPD) with increasing concentrations of ketoconazole, revealing a specific requirement for Gal11p for ketoconazole resistance; -, yeasts growing on YPD without ketoconazole.
Figure 2B:
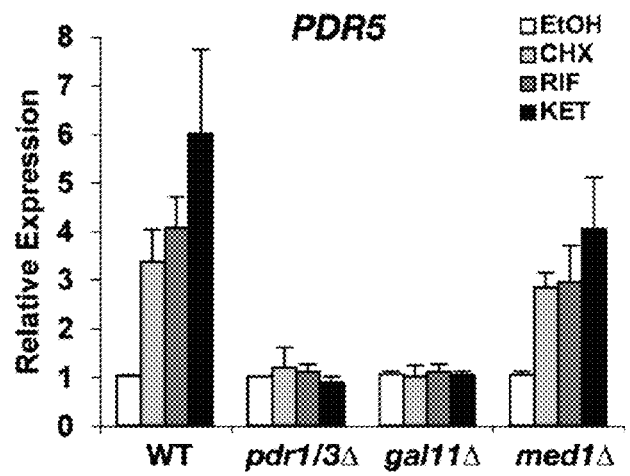
FIG. 2b, Gal11p is required for Pdr1p/Pdr3p-mediated and xenobiotic-dependent transcription of the PDR5 gene. Deletion of PDR1/3 was used as positive control. Real-time quantitative RT-PCR reactions were performed in triplicate. Mean values are shown; error bars, s.d.
Figure 2C:
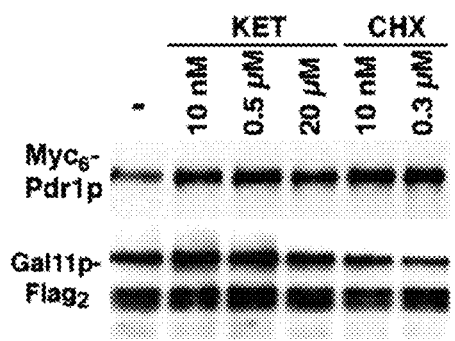
FIG. 2c, Co-immunoprecipitation shows the interaction between Myc$_6$-Pdr1p and Gal11p-Flag$_2$ in the absence and presence of different concentrations of ketoconazole and cycloheximide. Anti-Flag antibodies were used for immunoprecipitation, with IgG as negative control (no significant binding: data not shown). Anti-Myc (upper panel) and anti-Flag (lower panel) antibodies were used for immunodetection. There is no significant difference in the input material.

The Pdr1p/Pdr3p transcription factors require the Gal11p subunit of the Mediator co-activator for xenobiotic-dependent regulation of MDR. The Mediator co-activator plays critical roles in transcriptional activation, from yeast to human. Kornberg, 30 Trends Biochem. Sci. 235-39 (2005). Therefore, whether Mediator is involved in Pdr1p/Pdr3p-dependent and xenobiotic-stimulated gene activation and MDR was examined. Although deletion of most Mediator subunits caused few or modest effects on MDR, deletion of the gene encoding the Gal11p subunit resulted in striking sensitivity to several toxins/xenobiotics, including ketoconazole, cycloheximide and 4-nitroquinoline oxide (FIG. 2a and data not shown). Consistent with these findings, xenobiotic-dependent expression of the PDR5 and PDR16 genes was specifically and strongly decreased in the GAL11 deletion strain, similar to that observed with the PDR1/3 deletion strain (FIG. 2b and data not shown). Moreover, deletion of the GAL11 gene caused strongly decreased activation of the Pdr1p/Pdr3p-responsive promoters from the PDR5 and SNQ2 genes by constitutively active Pdr1p and Pdr3p mutants isolated from multidrug-resistant yeast (data not shown). Balzi et al., 1994; Kean et al., 138 J. Cell Bio. 255-70 (1997); Gulshan et al., 280 J. Biol. Chem. 40524-33 (2005). Co-immunoprecipitation experiments showed that $Myc_6$-Pdr1p interacts with Gal11p-$Flag_2$ in a xenobiotic-stimulated manner in vivo (FIG. 2c), and chromatin immunoprecipitation data indicate that Gal11p is specifically recruited to Pdr1p/Pdr3p target genes in a Pdr1p/Pdr3p-dependent fashion (data not show). These studies demonstrate that Gal11p is essential for xenobiotic-dependent gene activation and MDR mediated by Pdr1p/Pdr3p.

Figure 2D:
FIG. 2d, GST-pulldown analysis demonstrates increased interaction between the GST-Gal11p KIX domain and Myc$_6$-Pdr1p in the presence of activating xenobiotics. Bound Myc$_6$-Pdr1p was detected by anti-Myc immunoblotting.

Gal11p harbors an activator-binding KIX domain. Gal11p orthologs contain sequences in their amino termini that exhibit significant homology to the activator-binding KIX domain of the metazoan Mediator subunit ARC105/MED15. Novatchkova & Eisenhaber, 14 Curr. Biol. R54-R55 (2004); Yang et al., 442 Nature 700-04 (2006). The KIX domain was first identified as an activator target in the histone acetyltransferases CBP/p300, mediating interactions with many metazoan transcription factors. Goodman & Smolik, 14 Genes Dev. 1553-77 (2000). Based on the documented functional importance of the KIX domains in ARC105/MED15 and CBP/p300 in specific gene-activation pathways (Yang et al., 442 Nature 700-04 (2006); Kasper et al., 419 Nature 738-43 (2002); Kasper et al., 26 Mol. Cell. Biol. 789-809 (2006); Radhakrishnan et al., 91 Cell 741-52 (1997)), activators were identified in yeast that interact with the predicted Gal11p KIX domain. Remarkably, affinity chromatography of yeast whole-cell extract over the putative Gal11p KIX domain yielded a single specific band that was identified by mass spectrometry as Pdr1p, demonstrating that Pdr1p interacts strongly with the putative Gal11p KIX domain: the putative Gal11p KIX binds to purified Pdr1p and that this interaction is further enhanced by xenobiotics (FIG. 2d).

Figure 2E:
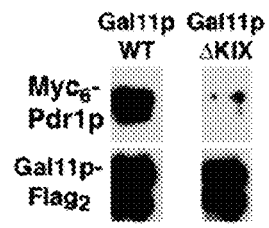
FIG. 2e, Co-immunoprecipitation shows the importance of the Gal11p KIX domain for in vivo interaction between Gal11p and Pdr1p. Yeast extracts from cells cultured in the presence of ketoconazole expressing Myc$_6$-Pdr1p and either Gal11p-Flag$_2$ or Gal11pΔKIX-Flag$_2$ were used for co-immunoprecipitation. Immunoprecipitation used anti-Flag antibodies; immunodetection used anti-Myc (upper panel) or anti-Flag (lower panel) antibodies.
Figure 2F:
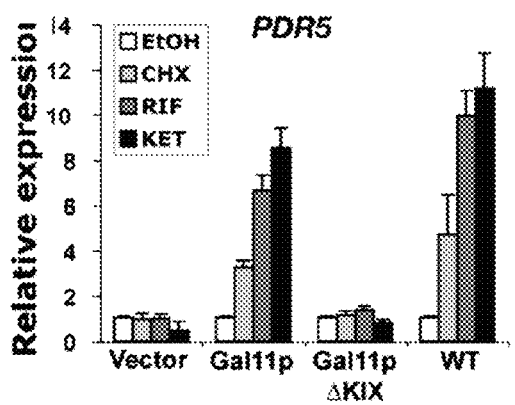
FIG. 2f, The Gal11p KIX domain is required for xenobiotic-induced transcription of PDR5. The gal11Δ yeast strain was reconstituted with plasmids expressing full-length Gal11p, or Gal11p lacking the KIX domain (amino acids 1-100), or with vector control. Wild-type yeast was used as positive control. Real-time quantitative RT-PCR reactions were performed in triplicate. Mean values are shown; error bars, s.d.
Figure 2G:
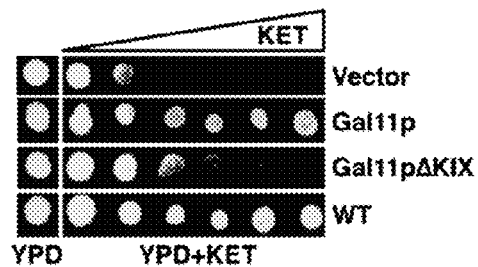
FIG. 2g, Growth of yeast cells on YPD with increasing concentrations of ketoconazole shows the requirement of the Gal11p KIX domain for ketoconazole resistance. The gal11Δ yeast strain was transformed with plasmids harboring either full-length Gal11p, Gal11p lacking the KIX domain (amino acids 1-100) or vector control. Wild-type yeast was used as positive control. Left panel shows yeast cells grown on YPD without ketoconazole.

Mapping studies revealed that C-terminal Pdr1p sequences containing the activation domain (Pdr1pAD) bind to the Gal11p KIX domain (data not shown). Interestingly, Pdr1pAD also bound to the CBP and ARC105/MED15 KIX domains. Consistent with its ability to engage mammalian co-activators, Pdr1pAD fused to Gal4pDBD mediated potent gene activation in human cells (data not shown). The Gal11p KIX domain can also interact with the human SREBP-1a activator that we previously showed associates with the ARC105/MED15 and CBP KIX domains (data not shown). Yang et al., 442 Nature 700-04 (2006); Näär et al., 12 Genes Dev. 3020-31 (1998). In contrast, the CBP/p300 KIX binding activators CREB and c-Myb cannot interact with the Gal11p KIX domain, nor with the human ARC105/MED15 KIX domain (data not shown). Yang et al., 442 Nature 700-04 (2006); Dal et al., 10 Genes Dev. 528-40 (1996); Zor et al., 337 J. Mol. Biol. 521-34 (2004). These results indicate that the putative Gal11p KIX domain is a specific target only for certain activators, and functionally behaves more like the human ARC105/MED15 KIX domain than the CBP KIX domain, in keeping with the fact that both ARC105/MED15 and Gal11p are components of the Mediator family of co-activators. The present invention also provides for the functional importance of the Gal11p KIX domain for Pdr1p/Pdr3p gene activation and MDR in vivo. Deletion of the Gal11p KIX domain strongly decreased interaction of Gal11p with Pdr1p in co-immunoprecipitation experiments (FIG. 2e). Moreover, exogenous expression of wild-type Gal11p, but not KIX-deleted Gal11p, can rescue both xenobiotic-dependent activation of Pdr1p/Pdr3p target genes and resistance to ketoconazole in yeast deleted for GAL11 (FIGS. 2f, 2g).

To provide molecular details that could yield further insights into the gene activation mechanism by Pdr1p, the solution structure of the Gal11p Pdr1p-binding domain was determined by NMR. The high-resolution structure reveals a three-helix bundle fold with marked similarity to the human ARC105/MED15 and mouse CBP KIX domains (FIGS. 3a, 3b). Yang et al., 2006; Radhakrishnan et al., 1997. Like the mammalian KIX domains, the three helices in the Gal11p KIX domain pack an extensively hydrophobic core. In the ARC105/MED15 and CBP KIX structures, hydrophobic patches on the surface of the KIX domains mediate interactions with several activators. Yang et al., 2006; Radhakrishnan et al., 1997; Zor et al., 2004. Chemical shift analysis showed that peptides containing the C-terminal 12 and 34 amino acids of the Pdr1pAD also interact with amino acids within a large hydrophobic groove contributed by all three helices, including L25, Q26, M29, I31, 134, A42, I47, N51, F52, A55, V74, A75 and V76 (FIG. 3d).

Binding studies of Pdr1p with point-mutated Gal11p KIX proteins in the presence of ketoconazole also revealed several KIX amino acids as being important for Pdr1p binding, consistent with the NMR data (FIG. 3d-f). NMR showed that yeast Pdr1pAD-34 can also interact with the human ARC105/MED15 KIX domain, consistent with the binding of a larger Pdr1pAD fragment (data not shown). Analysis by chemical shift perturbation revealed that the Pdr1p activation domain interaction surface on the Gal11p KIX domain substantially overlaps with that of the human SREBP-1a activation domain (data not shown). These results suggest similarities in the way activators target orthologous KIX domains. There are also significant differences, however, in the way Pdr1p and SREBP-1a engage their cognate KIX domains. These results agree with earlier observations that different activation domains (for example CREB pKID, c-Myb and MLL) bind both overlapping and distinct epitopes on the human ARC105/MED15 and mouse CBP KIX domains. Yang et al., 2006; Radhakrishnan et al., 1997; Zor et al., 2004; De Guzman et al., 355 J. Mol. Biol. 1005-13 (2006); Goto et al., 277 J. Biol. Chem. 43168-74 (2002); Parker et al., 2 Mol. Cell 353-59 (1998); Radhakrishrian et al., 287 J. Mol. Biol. 859-65 (1999). Thus, although the structure of the KIX domain is conserved between mammals and yeast, a variety of interfaces on KIX domains are used to accommodate various activation domains. Taken together, these findings reveal that the activator-binding domain in Gal11p indeed folds into a functionally conserved KIX domain; they also pinpoint key residues in the Gal11p KIX domain involved in binding to the Pdr1p activation domain.

Conservation of xenobiotic gene regulation in *C. glabrata*. Having dissected the molecular mechanisms underpinning the xenobiotic gene regulatory network controlling MDR in the non-pathogenic yeast *S. cerevisiae*, the potential clinical relevance of these findings for pathogenic fungi were determined. *C. glabrata* is the second most common cause of invasive candidiasis, and has been reported to exhibit intrinsic MDR, in particular to azoles. Ptaller & Diekerna, 20 Clin. Microbiol. Rev. 133-63 (2007); Prasad, 6 Infect. Discov. Drug Targets 69-83 (2006); Pfaller al., 45 Clin. Microbiol. 1735-45 (2007). *C. glabrata* harbors a highly conserved Pdr1p ortholog that also regulates drug efflux pumps in response to xenobiotics. Tsai, 2006; Vermitsky et al., 2006. Based on the present results with Pdr1p/Pdr3p in *S. cerevisiae*, CgPdr1p might also bind directly to azoles and other xenobiotics to promote gene expression and MDR in *C. glabrata*.

Figure 4A:
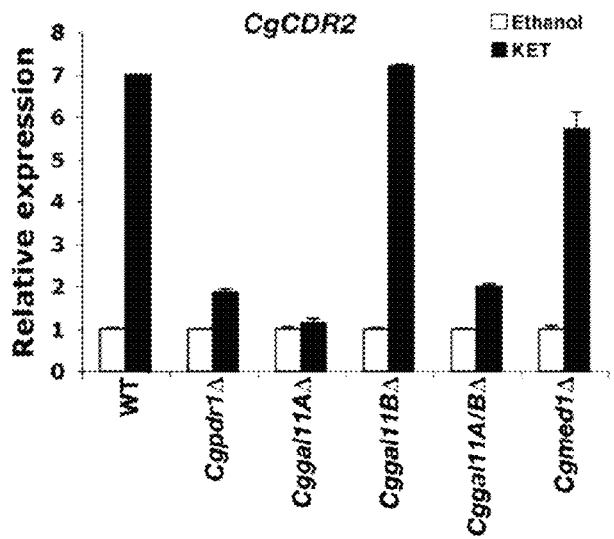
FIG. 4a, CgPdr1p and CgGal11Ap are required for ketoconazole-induced transcription of CgCDR2. Wild-type and Cgmed1Δ strains were used as controls. Real-time quantitative RT-PCR reactions were performed in triplicate. Mean values are shown; error bars, s.d.
Figure 4B:
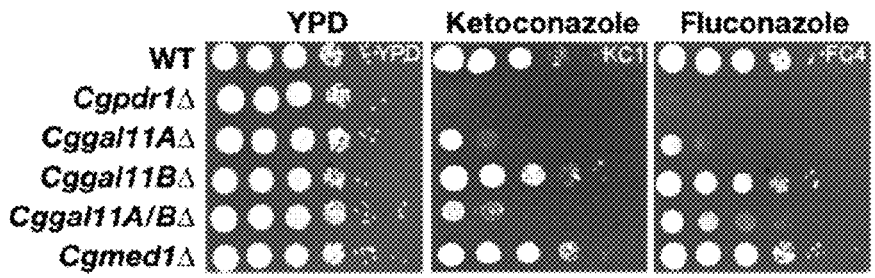
FIG. 4b, Growth of wild-type or mutant *C. glabrata* cells on YPD containing either ethanol vehicle (YPD), ketoconazole (1 µgml$^{-1}$; KCl) or fluconazole (4 µgml$^{-1}$; FC4) shows that CgPdr1p and CgGal11Ap are required for azole resistance in *C. glabrata*.
Figure 4C:
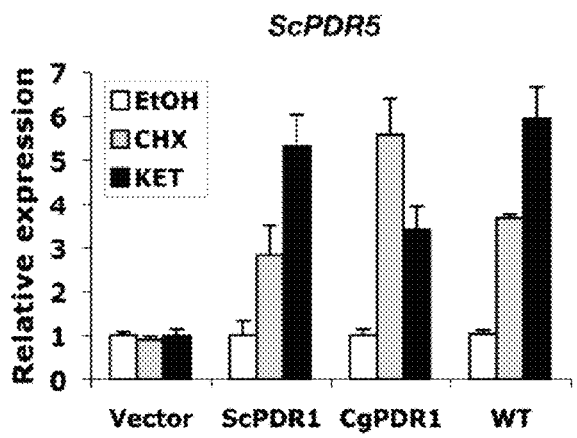
FIG. 4c, CgPdr1p can functionally complement ScPdr1p/Pdr3p for drug-induced PDR5 transcription. *S. cerevisiae* pdr1/3Δ double-deletion mutant strains transformed with plasmids harboring either ScPDR1 or CgPDR1 cDNA or vector were used for this assay. Real-time quantitative RT-PCR reactions were performed in triplicate. Mean values are shown; error bars, s.d.
Figure 6:
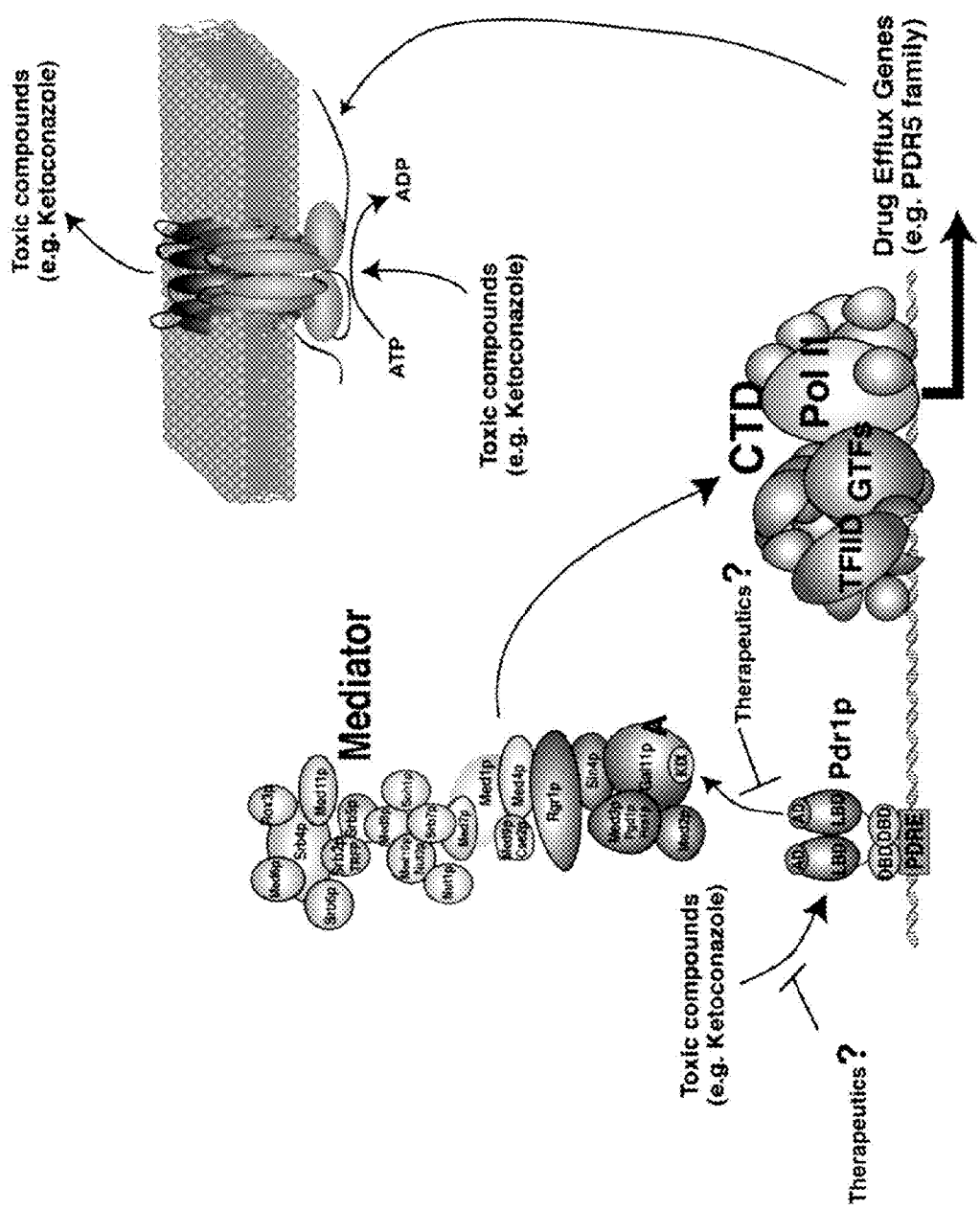
FIG. 6 is a cartoon depicting a hypothetical model of xenobiotic-dependent gene regulation of drug efflux pumps by Pdr1p orthologs in fungi. Pdr1p orthologs control the expression of genes encoding drug efflux pumps (e.g. ABC transporters) in response to direct binding of xenobiotics (e.g. ketoconazole) to a discrete ligand binding domain (LBD), allowing the activation domain (AD) to interact with the KIX domain of the Gal11p subunit of the Mediator co-activator. Mediator in turn interacts with the C-terminal domain (CTD) of the large subunit of RNA polymerase II (Pol II) and facilitates recruitment of Pol II to Pdr1p target genes, allowing transcription. Based on the nuclear receptor paradigm (e.g. the identification of tamoxifen as an antagonist of estrogen receptor signaling in breast cancer treatment), we speculate that small-molecule inhibitors might be identified that interfere with either productive xenobiotic binding or with Gal11p KIX recruitment by Pdr1p orthologs in pathogenic fungi. Such agents could serve as precursors for therapeutics targeting the molecular basis for xenobiotic-stimulated MDR in the prevalent human pathogen C. glabrata.

Expression of the *C. glabrata* drug efflux pump gene CDR2 is stimulated by xenobiotics in a CgPdr1p-dependent manner, and CgPdr1p is required for the intrinsically high azole resistance of *C. glabrata* (FIG. 4a, 4b). Tsai, 2996; Vermitsky et al., 2006. Complementation experiments in Pdr1/3-deleted *S. cerevisiae* were carried out to test whether expression of CgPdr1p in this strain could functionally substitute for *S. cerevisiae* Pdr1p/Pdr3p. Indeed, CgPdr1p expression rescued both xenobiotic-dependent gene activation and MDR to a similar extent as the expression of ScPdr1p, establishing the functional similarity of these transcription factors (FIG. 4c and data not shown). Importantly, like its *S. cerevisiae* orthologs, CgPdr1p binds directly to radiolabeled ketoconazole, indicating that CgPdr1p also acts by a direct effector mechanism akin to nuclear receptor signaling (FIG. 4d).

The co-activator requirements were examined for xenobiotic-dependent gene activation and MDR in C. glabrata. Interestingly, C. glabrata harbors two distinct genes with significant sequence similarity to the S. cerevisiae GAL11 gene (termed CgGAL11A and CgGAL11B here). Deletion of the CgGAL11A gene strongly decreased xenobiotic-dependent activation of the drug efflux gene CgCDR2, similar to the effects of deleting CgPDR1, whereas deletion of the CgGAL11B gene had no effect on CgCDR2 expression (FIG. 4a). CgGAL11A deletion also abrogated MDR, causing markedly increased sensitivity to azoles such as ketoconazole and fluconazole, as well as to cycloheximide, as revealed by growth assays (FIG. 4b and data not shown). The CgGAL11A/B double-deletion strain also performed like the CgGAL11A deletion strain (FIGS. 4a, 4b); these data suggest that CgGal11Ap is functionally more important in CgPdr1p xenobiotic-dependent gene activation than CgGal11Bp. Consistent with this notion, a CgPdr1p activation domain fragment interacts better with the CgGal11Ap KIX domain than with the CgGal11Bp KIX domain (data not shown).

Non-mammalian hosts, such as the nematode *Caenorhabditis elegans*, have recently been shown to provide powerful and facile model systems to investigate fungal pathogenicity, MDR mechanisms, host response pathways and to identify novel antifungals. Mylonakis & Aballay, 73 Interactions. Infect. Immun. 3833-41 (2005); Breger et al., 3 PLoS Pathogens e13 (2007). Infection of *C. elegans* with *C. glabrata* and other *Candida* species results in the death of most nematodes within six days, even in the presence of the antifungal fluconazole (FIG. 4e). Breger et al., 2007. The deletion of CgPDR1, CgGAL11A, CgGAL11B or CgMED1 had little effect on the pathogenicity of *C. glabrata* in this model organism in the absence of antifungals. By contrast, in the presence of fluconazole, nematodes infected with the Cgpdr1 and Cggal11A deletion strains exhibited significantly increased survival (FIG. 4e). *C. elegans* infected with the Cggal11B or Cgmed1 deletion strains showed little difference in survival rates in the presence of fluconazole, similar to wild-type *C. glabrata*. These results are consistent with the in vitro findings and demonstrate a critical role for the functional interaction of CgPdr1p and CgGal11Ap in *C. glabrata* MDR in vivo in a fungal pathogenesis model.

Fungi harbor sensor/effector regulatory mechanisms governing detoxification response that exhibit intriguing functional similarities to vertebrate nuclear xenobiotic receptors. Pdr1p orthologs and PXR both bind directly to structurally unrelated xenobiotics and drugs. As a result, they activate the expression of genes encoding ATP-dependent drug efflux pumps (for example P-glycoprotein/MDR1 orthologs). Kliewer et al., 2002. Bioinformatics studies based on the conservation of the zinc finger DNA-binding domain and the ligand-binding domain have shown that nuclear receptors first arose during metazoan evolution. Bertrand et al., 21 Mol. Biol. Biochem. 1923-37 (2004). Functional similarities of fungal Pdr1p orthologs and vertebrate PXR do not constitute proof of evolutionary orthology, however. Taken together with a recent study showing that the yeast zinc-cluster family member Oaf1p may function similarly to the vertebrate PPARα nuclear receptor (Phelps et al., 103 P.N.A.S. 7077-81 (2006)), further studies of mechanistic analogies (and possible evolutionary relationships) between fungal zinc-cluster transcription factors and metazoan nuclear receptors may be warranted.

The present invention reveals that fungal Pdr1p orthologs interact physically and functionally with the Gal11p/MED15 subunit of the Mediator co-activator. The present invention reveals that Gal11p harbors an activator-binding domain with marked structural similarity to KIX domains present in metazoan co-activators, indicating strong evolutionary conservation, which implies critical functionality. Interestingly, a recent study showed that the *C. elegans* nuclear receptor NHR-49 interacts with the KIX-containing Gal11p ortholog MDT-15 and requires MDT-15 for activation of fatty-acid metabolism genes. Taubert et al., 20 Genes Dev. 1137-49 (2006). This raises the question of whether other metazoan nuclear receptors also use the ARC105/MED15 subunit as a transducer of gene-activating signals. The targeting of ARC105/MED15 orthologs in fungi and metazoans might thus represent an ancient mechanism of activation by ligand-dependent transcription factors.

The elucidation of the molecular mechanism of xenobiotic-dependent regulation of MDR by CgPdr1p in *C. glabrata* provides novel targets for the development of "co-therapeutics" that augment standard antifungal therapies by interfering directly with the mechanistic underpinnings of antifungal-induced MDR. For example, small-molecule antagonists can now be identified that lock Pdr1p orthologs in an inactive conformation, thereby preventing activation of the efflux pump genes and resulting in sensitization to standard antifungal therapy. Alternatively, the highly hydrophobic groove in the Gal11p domain that provides the Pdr1pAD docking site serves as a therapeutic target. The present invention provides the foundation for studies investigating whether similar regulatory mechanisms govern MDR in other clinically significant pathogenic fungi, such as *C. albicans*.

The present invention provides for a novel mechanistic understanding of transcriptional control of MDR in fungi, and provides for high-throughput screens to identify specific antagonists/inhibitors of the *C. glabrata* MDR gene regulatory circuitry; such small-molecule inhibitors may prove useful in the molecular dissection of xenobiotic-dependent transcriptional regulation and may facilitate the identification of therapeutic agents to combat multidrug resistant *C. glabrata* infections.

Figure 7:
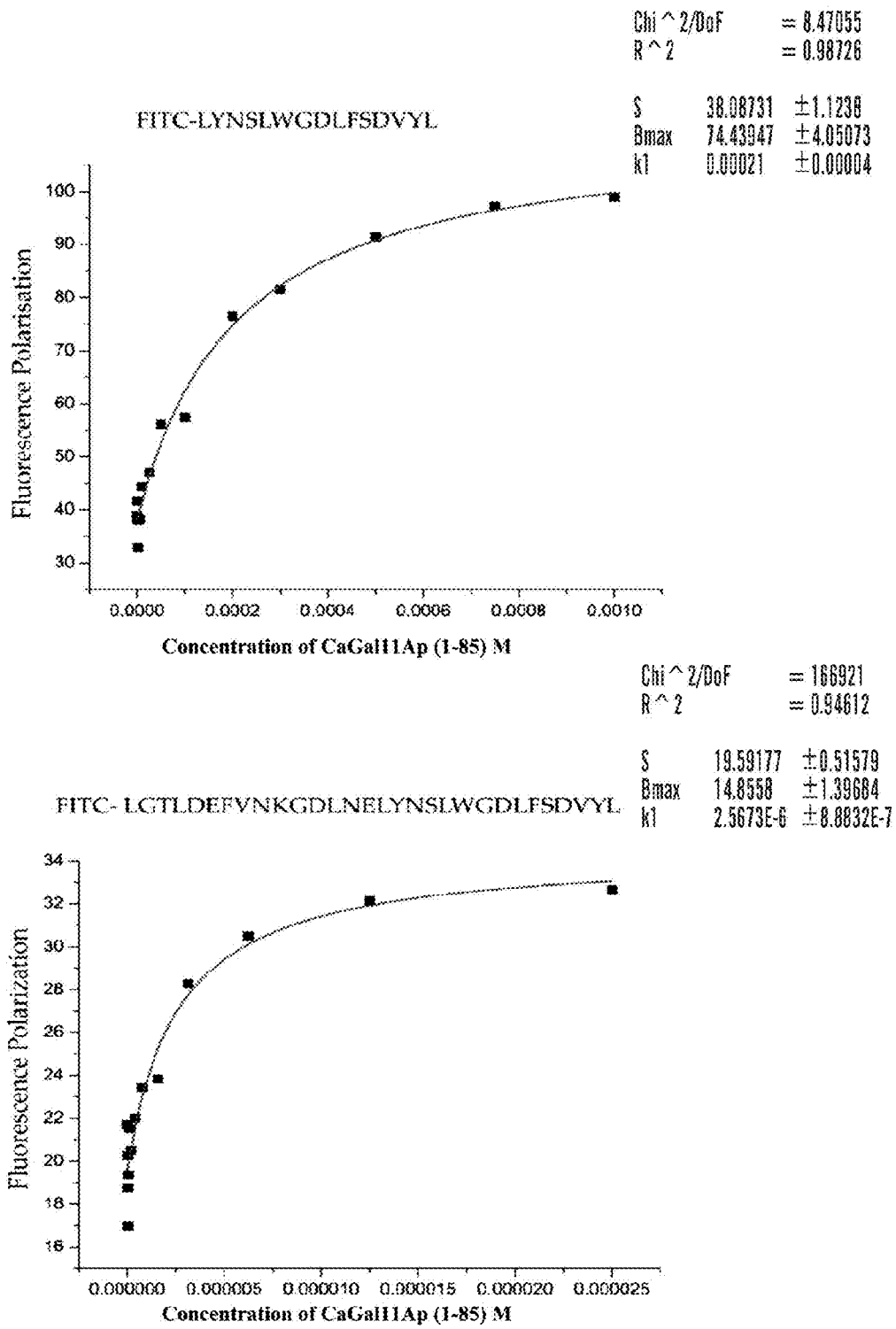
FIG. 7 shows binding curves of FITC-labled-CgPdr1pAD-12 (in 7a) and of FITC-labled-CgPdr1pAD-30 (in 7b) with increasing concentrations of GST-tagged CgGal11Ap-KIX domain. The binding constant was estimated to be 210 µM and 2 µM, respectively.
Figure 8A:
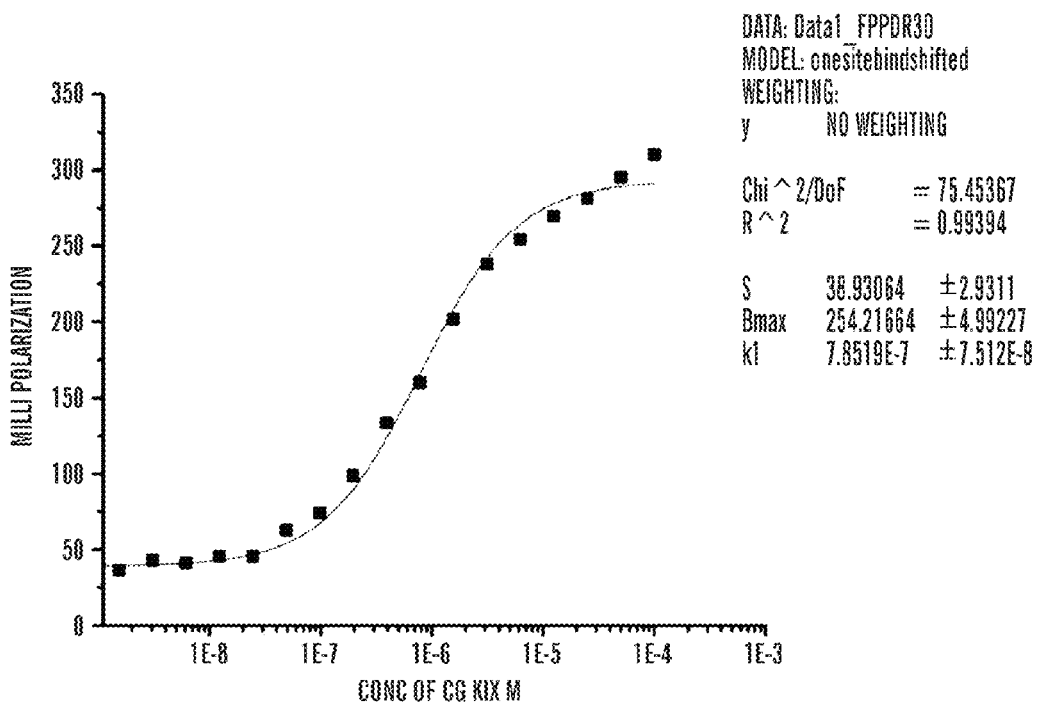
FIG. 8a presents a binding curve of FITC-labled-CgPdr1pAD-30 with increasing concentrations of GST-tagged CgGal11Ap-KIX domain. The binding constant is estimated to be ~780 nM.
Figure 8B:
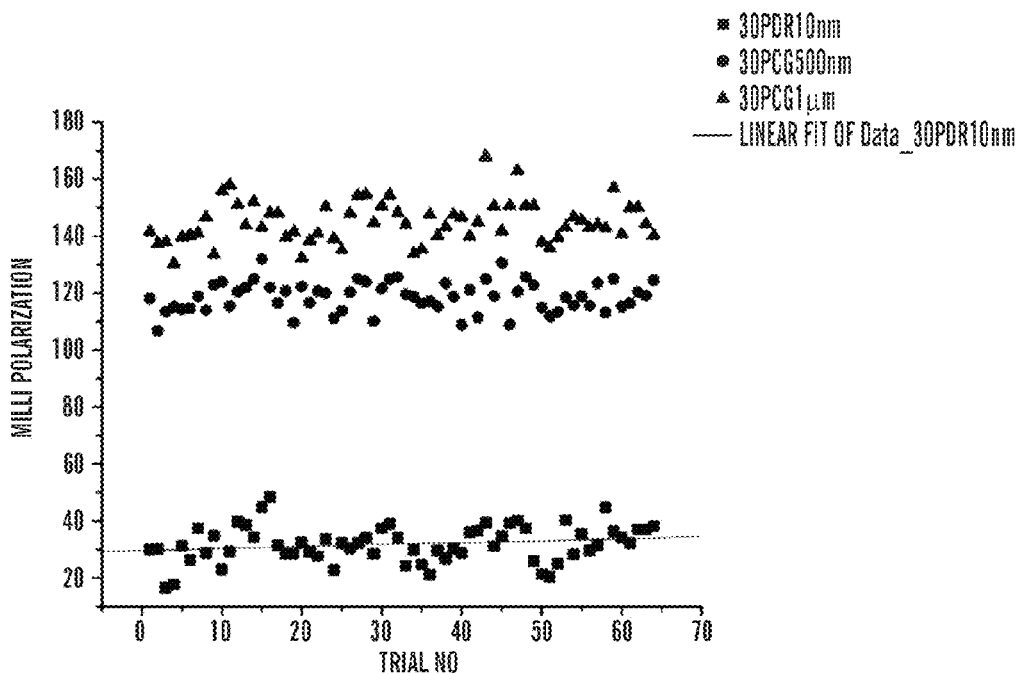
FIG. 8b shows Z-score test, ensuring the fidelity of the assay. Fluorescence polarization measurements are repeated for: (1) FITC-labeled CgPdr1pAD-30 peptide alone (squares); (2) FITC-labeled CgPdr1pAD-30 peptide with 500 nM GST-tagged CgGal11Ap-KIX domain (circles); and (3) FITC-labeled CgPdr1pAD-30 peptide with 1 µM GST-tagged CgGal11Ap-KIX domain (triangles) in multiple repetitions. The Z-score was 0.92, indicative of an excellent signal to noise level in the screen.

In one embodiment, the high throughput screening is a fluorescence polarization assay that comprises a fluorescein-tagged Pdr1pAD or a portion thereof, such as a 30-mer peptide derived from the CgPdr1pAD. The portion of the Pdr1pAD used is derived from the C-terminal portion of Pdr1p activation domain, which binds to the Gal11p KIX domain (or a portion thereof). The portion of the Pdr1pAD may be made synthetically. The portion of Pdr1pAD useful in the present invention may be 10 to 40 amino acids in length, inclusive. In a particular example, the fluorescein-tagged Pdr1pAD is a FITC-CgPdr1pAD30 (see FIG. 7). This embodiment also comprises a Gal11Ap KIX domain, such as a CgGal11Ap KIX domain, which may be tagged with glutathione S-transferase (GST) to increase the molecule's size and enhance polarization. Polarization data reflecting the binding of FITC-CgPdr1pAD30 with GST-tagged CgGal11Ap-KIX domain is shown in FIG. 8. This assay may be automated in embodiments of the present invention.

In another embodiment, the high throughput screen is a luminescence assay. More specifically, pdr1Δ pdr3Δ *S. cerevisiae* expressing CgPdr1p or wild type *C. glabrata* strains bearing the luciferase gene under the control of pleiotropic drug response element motifs (PDREs) are used to examine the effects of small-molecule inhibitors in down-regulating PDRE-dependent transcription (FIG. 5). A strain with luciferase under the control of oleic acid-response elements (ORE) is used in parallel; because ORE transcriptional activation is also Gal11p KIX domain-dependent, thus use of this control strain distinguishes compounds that specifically disrupt the Pdr1pAD-Gal11p KIX interaction interface. After cells are grown in the presence of the test drug, D-luciferin is added and luminescence read. This assay may be automated in embodiments of the present invention.

EXAMPLES

Example 1

Media and Chemicals; Strains and Plasmids

All bacteria were routinely grown in Luria-Bertani broth medium with required antibiotics. *S. cerevisiae* cells were grown either in YPD or in synthetic defined medium as required. For culturing *C. glabrata*, we used YPD or synthetic complete medium. Sherman et al., METHODS IN YEAST GENETICS (Cold Spring Harbor Lab., Cold Spring Harbor, N.Y., 1986). Unless specified, all chemicals and drugs were purchased from Sigma. Anti-HA (F-7) and anti-c-Myc (9E10) antibodies were obtained from Santa Cruz Biotechnology, whereas anti-Flag M2 antibody was purchased from Sigma. Glutathione-, Protein A- and Protein G-Sepharose beads were obtained from Amersham Pharmacia Biotech.

*Escherichia coli* strains DH5α and DH10 were used for all plasmid maintenance and construction. Yeast transformation was performed using a standard LiCl method. Gietz et al., 20 Nucleic Acids Res. 1425 (1992). All *C. glabrata* deletion strains were derived from our wild-type laboratory strain BG2 or from a ura3 derivative of BG2, BG1453. Cormack & Falkow, 151 Genetics 979-87 (1999). Gal4pDBD-Pdr1p or GST-Pdr1p fusion constructs were generated by cloning PCR fragments of PDR1 of specified size and region, into pGBKT7 (Clontech) or pGEX2-TKN in frame with Gal4pDBD or GST, respectively, using NcoI and NotI restriction sites. Yeast constructs expressing C-terminal Flag-tagged full-length Gal11p (Gal11p-Flag$_2$) or Gal11p with deletion of the KIX domain (amino acids 1-100) (Gal11Ap KIX-Flag$_2$), and N-terminal Myc-tagged full-length wild-type Pdr1p (Myc$_6$-Pdr1pwt), were generated by subcloning the PCR products into the plasmids pCU416 and pCU315; respectively. DNA fragments encoding CgGal11p KIX domains (CgGal11Ap (amino acids 1-86) and CgGal11Bp (amino acids 1-82)) were amplified by PCR from genomic DNA and subcloned into pGEX-2TKN. Point-mutated pGEX-2TKN-Gal11pKIX (amino acids 1-100) plasmids were produced using the Quickchange XL site-directed mutagenesis kit (Stratagene).

The mammalian constructs expressing HA-Gal4pDBD activation domains of ScPdr1p, ScPdr3p, ScGal4p and CgPdr1p were generated by subcloning the PCR products into pcDNA3-HA-Gal4pDBD using BamHI and EcoRI sites, All plasmids were confirmed by DNA sequencing.

Example 2

*C. glabrata* Strain Construction

The DNA sequences of the *C. glabrata* genes PDR1 (CAGL0A00451g), GAL11A (CAGL01106215g), GAL11B (CAGE0F00803g) and MED1 (CAGL0D01386g) were taken from the Genolevures website (see Thakur et al., 2008), and used to design primers for construction of disruption constructs and restoration constructs. Disruption constructs for *C. glabrata* genes are derived from pAP599 in which an hph expression cassette from 5' to 3', a 500 base pair (bp) *S. cerevisiae* PGKI promoter followed by *Klebsiella pneumoniae* hph coding sequences (CD Ss) and a 400 bp *S. cerevisiae* HIS3 3' untranslated region (UTR) that confers hygromycin B resistance (Hyg$^R$) is immediately flanked by *S. cerevisiae* FRT sites and then by multiple cloning sites (MCSs). A 0.5-1 kilobase (kb) 5' UTR and a 0.5-1 kb 3' UTR fragment of the target *C. glabrata* gene were amplified from BG2 genomic DNA by PCR and individually subcloned into pAP599. The accuracy of the cloned fragments was verified by DNA sequencing. The disruption construct containing the target gene 5' and 3' UTRs flanking the hph expression cassette was released from the gene disruption plasmid by restriction digest and used to transform BG14 to Hyg$^R$. The correct gene disruption was confirmed by PCR amplification. The hph expression cassette was then removed by transformation of the strains with a self-replicating plasmid, pRD16, that carries an expression cassette for *S. cerevisiac* FLP1 (a 2.5 kb *C. glabrata* EPA1 promoter followed by the *S. cerevisiae* FLP1 coding region). The Flp1 recombinase recognizes the FRT sites immediately flanking the integrated hph expression cassette and releases the cassette. pRD16 was subsequently lost by streaking cells on plates containing 5-FOA, which selects against URA3. The resulting strains (BG1710-1713) were then restored to Ura$^+$ by transforming yeast cells with PstI-digested pBC34.1, which carries an intact *C. glabrata* URA3 on a 4.1 kb PstI fragment to generate strains 1718-1721. gal11A gal11B double mutant was generated by disruption of GAL11B in strain BG1710.

TABLE 1

Example strains used

| Strain | Gentoype | Reference |
|---|---|---|
| WT BY4741 | MATa his3Δ1 leu2Δ0 met15Δ0 ura3Δ0 | Giaever et al. 2002 |
| WT SEY6210 | Matα leu2-3, -112 ura3-52 lys2-801 trp1-Δ901 his3-Δ 200 suc2-Δ9 Mel1 | Scott Emr |
| pdr1Δ | SEY6210 pdr1Δ | Scott Moye-Rowley |
| pdr3Δ | SEY6210 pdr3Δ | Scott Moye-Rowley |
| pdr1/3Δ | SEY6210 pdr1Δ pdr3Δ | Scott Moye-Rowley |
| yap1Δ | SEY6210 yap1Δ | Scott Moye-Rowley |
| rox3Δ | SEY6210 rox3Δ | Scott Moye-Rowley |
| gal11Δ | SEY6210 gal11Δ | Scott Moye-Rowley |
| med2Δ | SEY6210 med2Δ | Scott Moye-Rowley |
| rox3Δ | BY4741 rox3Δ | Kevin Struhl |
| med2Δ | BY4741 med2Δ | Kevin Struhl |
| nut1Δ | BY4741 nut1Δ | Kevin Struhl |
| ssn2Δ | BY4741 ssn2Δ | Kevin Struhl |
| srb8Δ | BY4741 srb8Δ | Kevin Struhl |

TABLE 1-continued

Example strains used

| Strain | Gentoype | Reference |
|---|---|---|
| cse2Δ | BY4741 cse2Δ | Kevin Struhl |
| ssn8Δ | BY4741 ssn8Δ | Kevin Struhl |
| pgd1Δ | BY4741 pgd1Δ | Kevin Struhl |
| med1Δ | BY4741 med1Δ | Kevin Struhl |
| soh1Δ | BY4741 soh1Δ | Kevin Struhl |
| sin4Δ | BY4741 sin4Δ | Kevin Struhl |
| srb5Δ | BY4741 srb5Δ | Kevin Struhl |
| gal11Δ | BY4741 gal11Δ | Kevin Struhl |
| CgBG2WT | Wild-type | Cormack & Falkow, 1999 |
| CgBG14 | ura3Δ::Tn903 G418$^R$ | Cormack & Falkow, 1999 |
| Cgpdr1Δ (BG1712) | ura3Δ::Tn903 G418$^R$ pdr1Δ | Herein |
| Cggal11AΔ (BG1710) | ura3Δ::Tn903 G418$^R$ gal11aΔ | Herein |
| Cggal11BΔ (BG1711) | ura3Δ::Tn903 G418$^R$ gal11bΔ | Herein |
| Cgmed1Δ (BG1713) | ura3Δ::Tn903 G418$^R$ med1Δ | Herein |
| Cggal11A/BΔ (BG1725) | ura3Δ::Tn903 G418$^R$ gal11aΔ gal11bΔ::hph Hyg$^R$ | Herein |
| Cgpdr1Δ (BG1719) | URA3 pdr1Δ | Herein |
| Cggal11AΔ (BG1718) | URA3 gal11aΔ | Herein |
| Cggal11BΔ (BG1721) | URA3 gal11bΔ | Herein |
| Cgmed1Δ (BG1720) | URA3 med1Δ | Herein |
| Cggal11A/BΔ (BG1726) | URA3 gal11aΔ gal11bΔ::hph Hyg$^R$ | Herein |

Example 3

Treatment of Yeast Cultures with Different Xenobiotics

Yeast cultures were grown overnight with agitation in YPD at 30° C. The next day, cells were pelleted and washed twice with sterilized purified water (Millipore). Cells were then resuspended in 1% yeast extract and 2% peptone (YP) to an optical density (OD$_{600}$) of 0.8, grown for another 16 hr at 30° C., then treated with different drugs for 20 min for quantitative RT-PCR, or 5 hr for β-galactosidase assay.

Example 4

Quantitative Real-Time RT-PCR

Total RNA was extracted from 5 ml of yeast culture using the Qiagen RNeasy MiniKit. Two micrograms of total RNA was used to generate cDNA using the First-Strand cDNA Synthesis Kit (GE Healthcare). The cDNA mix was diluted tenfold, and 2 μl was used for real-time quantitative PCR with SYBR Green (Applied Biosystems) on an ABI Prism 7900HT Sequence Detection System (Applied Biosystems).

TABLE 2

List of primers used for quantitative real-time RT-PCR

| | | |
|---|---|---|
| ScPDR5 | Forward | 5'ACTTCTGGATTGTTTGGCCG3' SEQ ID NO: 1 |
| | Reverse | 5'CTCAATGACTCCCTCACAGTGG3' SEQ ID NO: 2 |
| ScPDR16 | Forward | 5'AATAACTGCTGACTTGGTGGCC3' SEQ ID NO: 3 |
| | Reverse | 5'CCAACATGAAGACCAAGTGCTG3' SEQ ID NO: 4 |
| ScACT | Forward | 5'CTCCGTCTGGATTGGTGGTTCT3' SEQ ID NO: 5 |
| | Reverse | 5'CGCGCACAAAAGCAGAGATTA3' SEQ ID NO: 6 |
| CgCDR2 | Forward | 5'AAGGTGCCAAACAGAAAGGTGA3' SEQ ID NO: 7 |
| | Reverse | 5'TGGTCGCATTGGAGGTTATAGA3' SEQ ID NO: 8 |
| CgACT | Forward | 5'CTCCACCACTGCTGAAAGAG3' SEQ ID NO: 9 |
| | Reverse | 5'GGTCAATACCAGCGATTCTAG3' SEQ ID NO: 10 |

Example 5

β-Galactosidase Assay

Yeast culture (1.5 ml) was harvested by brief spinning. The pellet was resuspended in 300 μl of Z buffer (10 mM Na$_2$HPO$_4$.7H$_2$O, 10 mM NaH$_2$PO$_4$.7H$_2$O, 10 mM KCl, 1 mM MgSO$_4$.7H$_2$O, pH 7.0). One hundred microliters of this suspension was transferred to a fresh tube and subjected to three cycles of freeze (30 sec in liquid N$_2$) and thaw (1 min at 37° C.). After this, 0.7 ml of Z buffer with β-mercaptoethanol (0.27 ml β-mercaptoethanol in 100 ml of Z buffer) was added, immediately followed by addition of 160 11 of ONPG solution (4 mg ml$^{-1}$ in Z buffer). The tube was kept at 30° C. until yellow color developed, when 0.4 ml of 1 M $Na_2CO_3$ was added to stop the reaction. The cell debris was pelleted by centrifugation, and the supernatant was used to measure $OD_{420}$. All the readings were normalized to the concentration of protein (as determined by Bradford). All experiments were performed with three independent replicates.

Example 6

Drug Sensitivity Assays

Fresh *S. cerevisiae* colonies were inoculated in 5 ml of YPD or SD selection medium, and grown overnight at 30° C. The cells were diluted to an $OD_{600}$ of 0.2, and 2 µl were spotted on agar-based solid medium containing an increasing gradient of drugs (for example, ketoconazole, cycloheximide, or 4-NQO) in the agar. The plates were incubated at 30° C. for 2-3 days. Susceptibility of the *C. glabrata* mutants was tested by spotting serial dilutions of cells onto YPD agar plates supplemented with fluconazole or ketoconazole. The yeast strains were grown overnight at 30° C. in YPD liquid medium. Cells were diluted to an $OD_{600}$ of 2.0 in PBS, and 4 µl of the cell suspension and tenfold serial dilutions of the cells were spotted onto plates. Growth was assessed after 1 day of incubation at 30° C.

Example 7

Immunoprecipitation and Immunoblotting

For co-immunoprecipitation, yeast cells were transformed with $Myc_6$-Pdr1pwt and Gal11p-$Flag_2$ (or Gal11pAKIX-$Flag_2$). Cells were washed with 1×PBS after overnight culture in YPD medium, and then cultured in YP for another 24 hr. Cells were then treated with different concentrations of ketoconazole and cycloheximide (or ethanol for vehicle controls) for 1 hr. Yeast cell lysates were extracted in immunoprecipitation buffer (50 mM Tris-HCl, pH 8.0, 140 mM NaCl, 0.1 mM EDTA, 10% glycerol, 0.02% NP-40, 1 mM DTT, 0.25 mM PMSF, 1 mM benzamidine, 0.5 $mgml^{-1}$ aprotinin and Protease Inhibitor Cocktail (Complete, Roche)), with or without xenobiotics by vortexing in the presence of glass beads. The Flag-tagged proteins were then immunoprecipitated by adding anti-Flag M2 antibody-beads (Sigma) and incubating for 3 hr with mutating at 4 C. After washing five times with 1 ml of 0.25 M KCl IP buffer, bound proteins were eluted with 0.1 $mgml^{-1}$ Flag peptide (Sigma). Xenobiotics at the indicated concentrations were present at all steps of the co-immunoprecipitation, including washing. Immunoblotting was performed according to standard protocols. To immunopurify $Myc_6$-Pdr1pwt or HA-Pdr1pwt, yeast whole-cell extract (in immunoprecipitation buffer) was incubated with anti-Myc (9E10) antibody or anti-HA (F-7) antibody, and a 50% mix of Protein A- and G-Sepharose beads (Amersham) at 4° C. for 3 hr. Beads were washed with IP buffer five times, and used for drug-binding experiments as outlined herein.

Example 8

Chromatin Immunoprecipitation

Chromatin immunoprecipitation was performed according to standard procedures. Aparicio, 24 Mol. Cell. Biol. 4769-80 (2004). Briefly, yeast cells were grown to an $OD_{600}$ of 0.8 before fixing with 1% formaldehyde for 20 min. The cells were washed with Tris-buffered saline (20 mM Tris-HCl, pH 7.5, and 150 mM NaCl), and resuspended in 1 ml of FA lysis buffer (50 mM HEPES, pH 7.5, 150 mM NaCl, 1 mM EDTA, 1% Triton X-100, 0.14% sodium deoxycholate and 0.1% SDS). Cells were lysed using soda lime 0.5 mm glass beads and Beadbeater (BioSpec Products). The glass beads were then removed and the cell debris with chromatin was subjected to sonication (550 Sonic Dismembrator, Fisher) two times for 30 sec each, separated by incubation for 2 min on ice. The soluble chromatin was collected in a fresh tube. Chromatin (300 µl) was used for immunoprecipitation with anti-HA Ab and Protein A-Sepharose beads (Amersham), and the immunoprecipitated chromatin was eluted with 200 µl of 0.5 $mgml^{-1}$ HA peptide (Sigma) in Tris-buffered saline. Input and immuno-precipitated chromatin were decrosslinked at 65° C. overnight, and then passed through a Qiagen PCR purification column. The purified DNA was analyzed by quantitative PCR in real-time using the ABI Prism 7900HT Sequence Detection System (Applied Biosystems). Relative occupancy values were calculated by determining the apparent immunoprecipitation efficiency and normalized to the level observed at an open reading frame (ORF)-free region from chromosome V.

Example 9

Drug-Binding and Cold Competition Assay

Xenobiotic-binding experiments were performed essentially as described (Kapinsky & Lasar, 435 Nature 446-51 (2005)), with some modifications as explained herein. Radio-labelled ketoconazole (KET: [$^3$H]G), specific radioactivity 10 Ci $mmol^{-1}$, was purchased from American Radiolabelled Chemicals. Beads with either immunopurified proteins or GST recombinant proteins were incubated with KET ([$^3$H]G) in drug-binding buffer (10 mM $K_2HPO_4$, 10 mM $KH_2PO_4$, pH 7.0, 2 mM EDTA, 50 mM NaCl, 1 mM DTT, 0.5 mM CHAPS, 10% glycerol and protease inhibitors) at 4° C. for 3 hr with mixing in a volume of 500 µl. For cold competition, unlabelled xenobiotics were added to a concentration of 1,000-fold excess of KET. The beads were then washed thrice briefly, in 900 µl of ice-cold drug-binding buffer, carefully removing as much of each wash as possible. The washed beads were resuspended in 100 µl of drug-binding buffer, added to 5 ml of scintiliation fluid Aquasol-2 (Perkin Elmer) and mixed briefly by shaking. After 10 min, scintillation counting was performed in a 156500 Multi-Purpose Scintillation Counter (Beckman Coulter). All experiments were performed with at least three replicates.

Example 10

GST Fusion Proteins and GST Pull-Down Assays

Recombinant GST-fusion proteins were expressed in *E. coli* (BL21, DE3) and purified using glutathione-Sepharose beads according to standard protocol (Pharmacia). Two (2) ml of overnight-grown bacterial culture was inoculated in 1 L of LB with antibiotic selection, and incubated at 37° C. with shaking at 200 rpm until $OD_{600}$ was approximately 0.7. Expression of recombinant GST-fusion protein was induced with 250 µM IPTG for 3 hr. The cells were harvested and resuspended in EB (0.5 M NaCl, 20 mM Hepes, pH 7.6, 0.5 mM EDTA, 10% glycerol, 0.5% NP-40, 1 mM DTT, 0.25 mM PMSF, 1 mM benzamidine, 2 µg/ml aprotinin), and sonicated (550 Sonic Dismembrator, Fisher Scientific) three times for 20 sec, each. The lysate was centrifuged at 15,000 rpm for 30 min. The supernatant was incubated with 200 µl of glutathione-sepharose beads pre-equilibrated with EB for 1 hr at 4° C. The beads were then washed three times with W1 (EB with 1 M NaCl and 1% NP-40), five times with EB, and once with W2 (0.1 M KCl, 20 mM Hepes, pH 7.6, 0.1 mM EDTA, 10% glycerol, and 0.02% NP-40, 1 mM DTT, 0.25 mM PMSF, 1 mM benzamidine, 2 µg/ml aprotinin). The washed beads were resuspended in one bead-volume of W2.

Beads with GST proteins were incubated with either whole-cell lysate or in vitro translated protein in binding buffer (20 mM Tris-HCl, pH 8.0, 150 mM NaCl, 0.1 mM EDTA, 10% glycerol, 0.05% NP-40, 1 mM DTT, 0.25 mM PMSF, 1 mM benzamidine and Protease Inhibitor Cocktail (Roche)), for 3 hr at 4° C. The beads were washed five times with wash buffer (20 mM Tris-HCl, pH 8.0, 250 mM KCl, 0.1 mM EDTA, 10% Glycerol, 0.1% NP-40, 1 mM DTT, 0.25 mM PMSF, 1 mM benzamidine and Protease inhibitor Cocktail). The beads were finally washed once with binding buffer. The bound proteins were then eluted with 50 µl of 0.3% sarkosyl in binding buffer for 1 h at 4° C. The eluted proteins were resolved on 10% polyacrylamide gel and detected either by immunoblotting or by autoradiography.

Example 11

Large-Scale Purification and Identification of GST-Gal11p KIX-Associated Proteins in Yeast Yeast (6 L) cultured in YPD medium overnight was harvested by centrifugation and washing once with distilled water. The cell pellet was then resuspended in 0.25 volumes of lysis buffer (50 mM Tris-HCl (pH 8.0), 400 mM NaCl, 5 mM $MgCl_2$, 1 mM EGTA, 1 mM EDTA, 0.1% NP-40, 1 mM DTT, 0.25 mM PMSF, 1 mM benzamidine, 0.5 mgml$^{-1}$ aprotinin and Protease Inhibitor Cocktail (Complete, Roche), and the suspension was quick-frozen in liquid nitrogen. Frozen cells were lysed by grinding with a mortar and pestle together with dry ice. One volume of lysis buffer was added after evaporation with dry ice, and the extract was spun at 4,000 g for 10 min. The supernatant was pre-incubated with 200 µl glutathione-Sepharose-bound GST for 2 hr at 4° C. with rotation, then it was incubated for another 3 hr at 4° C. with 200 µl glutathione-Sepharose-bound GST-Gal11p KIX (amino acids 1-100). The beads were washed seven times with wash buffer (20 mM Tris-HCl, pH 8.0, 250 mM KCl, 0.1 mM EDTA, 10% glycerol, 0.1% NP-40, 5 mM $MgCl_2$, 1 mM EGTA, 1 mM EDTA, 1 mM DTT, 0.25 mM PMSF, 1 mM benzamidine and Protease Inhibitor Cocktail). The beads were finally washed once with low salt (150 mM NaCl) wash buffer. The bound proteins were then eluted with 500 µL of 0.3% sarkosyl in binding buffer for 1 hr at 4° C. and dialyzed overnight in 1 L of dialysis buffer (1% SDS, 1 mM β-mercaptoethanol and 1 mM Tris-HCl, pH 8.0). The dialyzed dilate was concentrated by dry-ice/ethanol SpeedVac to approximately 80 µl. The eluted proteins were resolved on 10% polyacrylamide gel and stained with Coomassie colloidal blue. The specific band at about 120 kDa was excised and subjected to trypsin digestion, followed by liquid chromatography MS/MS (LC-MS/MS) at the Taplin Biological Mass Spectrometry Facility at Harvard Medical School.

Example 12

C. Elegans Liquid Killing Assays

The C. glabrata strains and lawns were grown and prepared as described previously. Breger, 3 PloS Pathogens, e18 (2007). The liquid medium killing assays were conducted as detailed in Breger, 2007, with a few changes. After the glp-4;sek-I worms were incubated at 25° C. for 2 days, they were washed off the nematode growth medium plates with M9 and transferred to C. glabrata lawns formed on Brain-Heart Infusion broth (Difco) agar plates. The worms were incubated on the lawns for 4 hr at 25° C., then washed off the plates with M9 buffer and allowed to crawl on unneeded Brain-Heart Infusion broth plates to remove yeast cells from their cuticles. Approximately 70-80 worms were then picked to wells in a six-well microtiter dish that contained 2 ml of liquid medium of 79% M9 buffer, 20% Brain-Heart Infusion broth, 10 µgml$^{-1}$ cholesterol in ethanol, and 90 µgml$^{-1}$ kanamycin, with the addition of 0.25% DMSO or 8 µgml$^{-1}$ fluconazole. The plates were incubated at 25° C. overnight and then examined at 24 hr intervals for survival. Worms were considered dead and removed when they did not respond to being touched by a platinum wire pick. P values were calculated based on the entire six-day experiment with the log rank and Wilcoxon tests performed by STATA 6 statistical software (Stata, College Station, Tex.).

Example 13

Structural Analysis by NMR

A pET24b plasmid containing the Gal11p KIX sequence with an N-terminal His$_6$-tag followed by a cleavage site for the tobacco etch virus protease was transformed into E. coli BL21 (DE3) cells. The cells were grown to an OD$_{600}$ of 0.7 at 37° C. and induced for 12-16 hr at 25° C. with 1 mM isopropyl β-D-1-thiogalactopyranoside. The cells were lysed by sonication, centrifuged and the supernatant was purified by Ni-NTA resin (Qiagen). The His tag was cleaved off by Tev protease overnight at 4° C. This sample was further purified by fast protein liquid chromatography using a size exclusion column (Sephadex 75, Pharmacia). All NMR samples were in PBS buffer (10 Na$_2$HPO$_4$, 2 mM K$_2$HPO$_4$, 137 mM NaCl, 2.7 mM KCl, 1 mM EDTA and 0.01% NaN$_3$), pH 6.5, unless otherwise stated. Pdr1pAD-34 was expressed as a GST-fusion tag in E. coli BE21 (DE3) cells. The protein was purified as described above with the fusion tag cleaved after Ni-resin purification. $^{15}$N/$^{13}$C-labeled samples of Gal11 p KIX and Pdr1pAD-34 were obtained by overexpression of the respective proteins in M9 minimal media enriched with $^{15}$NH$_4$Cl and/or [$^{13}$C]glucose. Perdeuterated samples of Gal11p KIX were generated in similar fashion with the protein expressed in M9 minimal media in $^2$H$_2$O using [$^{13}$C-$^2$H] glucose. Pdr1pAD-12 (H$_4$N-EDLYSILWSDVY-COOH) (SEQ ID NO:11) and SREBP-1a-26 (H$_4$N-EPCDLDAALLTDIED-MLOLINNQDSD-COOH) (SEQ ID NO:12) were purchased as synthetic peptides from Tufts New England Medical Center peptide synthesis facility, Boston, Mass. Titrations with the peptide were performed in a "high phosphate buffer" (50 mM Na$_2$HPO$_4$, 50 mM NaH$_2$PO$_4$, 2 mM K$_2$HPO$_4$, 2.7 mM KCl, 1 mM EDTA and 0.01% NaN$_3$) to maintain the pH during the course of the titration.

For NMR spectroscopy, backbone assignments were mostly obtained by the standard set of triple resonance experiments (HNCA/HNCOCA, HNCACB/CBCACONH, HNCO/HINCACO). Ferentz & Wagner, 33 Q. Rev. Biophys. 29-65 (2000). Because the Gal11p KIX exhibited stretches that were difficult to assign, a time-shared (HA)CANH/(HN) NCAHA was used to verify and complete the backbone assignment. Frueh et al., 33 J. Biomol. NMR 187-96 (2005). The side-chain residues were assigned using HCCONH and CCONH experiments of Gal11p KIX in H$_2$O and HCCH-TOSY in $^2$H$_2$O. $^{15}$N-dispersed heteronuclear single-quantum coherence-nuclear overhauser enhancement spectroscopy (HSQC-NOESY) with a mixing time of 90 ms was recorded to provide distance constraints. All backbone experiments were performed on a Bruker 600 MHz spectrometer equipped with a cryoprobe. The side chain and NOESY experiments were performed on Bruker 500 MHz and 900 MHz spectrometers, respectively. Cross-saturation experiments were performed using perdeuterated samples of $^{15}$N-enriched Gal11p KIX and unlabelled Pdr1pAD-12. The methyl region (1 p.p.m.) was excited with a wideband uniform rate smooth truncation pulse for 2 sec, and this was followed by a standard HSQC experiment. The experiment was performed in an interleaved fashion with irradiation and no irradiation in successive scans. The ratio of intensities between the irradiated HSQC and the non-irradiated HSQC was later analyzed. Takahashi, 7 Nature Struct. Mol. Biol. 220-23 (2000). ARC105 KIX was expressed as a GST fusion protein and purified over a glutathione-Sepharose column. ARC105 KIX was cleaved from GST using tobacco etch virus protease. The cleaved protein was further purified by fast protein liquid chromatography using a size exclusion column (Sephadex 75, Pharmacia) in a buffer containing 30 mM NaCl, 5 mM $Na_2HPO_4$ and 5 mM $KH_2PO_4$ at pH 6.8. For titration experiments, unlabelled Pdr1pAD-34 was purified in the same buffer as mentioned above and added to ARC105 KIX.

For NMR Structure calculations, NMR structure refinement was performed using the program CYANA. Guntert et al., 273 J. Mol. Biol. 283-98 (1999). Torsion angle constrains (146 constrains) were calculated using the program TALOS. Cornilescu, 13 J. Biomol. NMR 289-302 (1999). Assignment of the backbone and side-chain resonances was performed using the program CARA, One thousand three hundred and fifty-nine distance restrains were calculated from the $^{14}$N-dispersed NOESY experiments. NOESY cross peaks were integrated using the program Peakint.

Example 14

High Throughput Luciferase Screen for Small-Molecule Antagonists of Xenobiotic-Dependent Gene Activation Mediated by the *C. glabrata* Pdr1p X-TAD

*C. glabrata* is a prevalent pathogen in immuno-compromised patients and exhibits high intrinsic multidrug resistance, posing a significant therapeutic challenge. Small-molecule antagonists of the xenobiotic binding function of CgPdr1p and inhibitors of the CgPdr1pAD interaction with CgGal11Ap KIX represent structural leads for novel "co-therapeutics", i.e., agents that inhibit CgPdr1p-mediated MDR and sensitize cells to the cytotoxic/cytostatic action of standard antifungal therapies, thereby increasing their efficacy. The present embodiments provide for a high-throughput screen for small-molecule antagonists of xenobiotic-dependent gene activation mediated by the *C. glabrata* Pdr1p X-TAD.

Studies have shown that the ligand binding function of nuclear receptors can be exploited to find antagonists that interact with the ligand binding domain (LBD) but which do not cause a conformational change allowing productive co-activator recruitment (and often cause co-repressor recruitment instead). Such antagonists are now used in the clinic to treat diseases associated with nuclear receptor dysfunction. For example, tamoxifen and faslodex are potent antagonists of the estrogen receptor, which is implicated in breast cancer cell proliferation, and these agents are actively used to treat breast cancer. Lewis-Wambi et al., 24 Breast Dis. 93-105 (2005). Similarly, bicalutamide (Casodex) is a potent androgen receptor antagonist employed in the treatment of prostate cancer. Culig, 170 J. Urol. 1363-69 (2003).

Because of the functional similarity of Pdr1p orthologs with PXR and their critical role in MDR, a high-throughput screen for small-molecule antagonists of xenobiotic-dependent transactivation by CgPdr1p was developed. Such antagonists ultimately serve as precursors for MDR-targeting therapeutics for the treatment of multidrug resistant *C. glabrata*. As discussed herein, a non-pathogenic heterologous model system for CgPdr1p function has been created, demonstrating that CgPdr1p can functionally replace Pdr1p/Pdr3p in *S. cerevisiae* in mediating xenobiotic-dependent induction of PDR5 transcription and promotion of MDR (see FIG. 4c). A reporter that harbors three pleiotropic drug response elements (PDREs) fused to the CYC1 promoter driving the expression of luciferase was generated, and integrated into the pdr1/3Δ strain expressing CgPdr1p. This luciferase reporter system was initially developed for the study of the estrogen receptor and its response to estrogenic compounds in yeast. Leskinen, 61 Chemosphere 259-66 (2005); Lekinen et al., 20 Yeast 1109-13 (2003). This reporter system recapitulates potent PDRE-dependent and xenobiotic-stimulated transcription (FIG. 5).

In this assay, pdr1Δ pdr3Δ *S. cerevisiae* or wild type *C. glabrata* bearing a PDRE-Luc reporter are grown overnight in SC-dextrose in a 200 rpm shaker at 30° C. The cultures are then inoculated to an $OD_{600}$ of 0.1 and incubated until growth reaches $OD_{600}$ 0.5. Aliquots of 25 µL of cells are inoculated into each well of a 384-well plate; each xenobiotic +/– small molecule is added (delivered in 25 µL SC-GLU media) and plates are incubated at 30° C. for 24 hr. Plates are shaken briefly, 50 µL of D-luciferin (Pierce) in 0.1M sodium citrate buffer pH 5 is added to each well and luminescence is read.

The luciferase system/protocol allows quantitative reading of luciferase activity over a broad dynamic range in live cells, obviating the need to perform protein extraction protocols, a critical advance that will facilitate high-throughput screening. This assay for high-throughput screening for small-molecule antagonists of xenobiotic response also allows for automated (robotic) screening. Diverse sets of chemical libraries, containing more than 200,000 unique small molecules, as well as natural product libraries, can be screened. This includes, for example, the Prestwick library (1,120 chemicals) of off-patent compounds selected for structural diversity, collective coverage of multiple therapeutic areas, and known safety and bioavailability in humans, as well as the NINDS Custom Collection 2 consisting of a 1,040 compound-library of mostly FDA-approved drugs (see Table 3 for a list of libraries).

TABLE 3

| ICCB Chemical Compound Libraries | |
|---|---|
| Library | Compounds |
| NINDS Custom Collection 2 | 1,040 |
| BIOMOL ICCB | 480 |
| Known Bioactives2 | |
| Prestwick1 Collection | 1,120 |
| ActiMol TimTec 1 | 8,518 |
| Asinex 1 | 12,378 |
| Bionet 1 | 4,800 |
| Bionet 2 | 1,700 |
| CEREP | 4,800 |
| Chembridge Microformat | 48,960 |
| Chembridge 3 | 10,560 |
| ChemDiv 1 | 28,864 |
| ChemDiv 2 | 8,560 |

TABLE 3-continued

ICCB Chemical Compound Libraries

| Library | Compounds |
|---|---|
| ChemDiv 3 | 16,544 |
| ChemDiv 4 | 14,677 |
| ChemDiv-Anti-Mitotic | 1,254 |
| Enamine 1 | 6,004 |
| Enamine 2 | 26,576 |
| I.F. Lab 1 | 6,543 |
| I.F. Lab 2 | 292 |
| Life Chemicals 1 | 3,893 |
| Maybridge 1 | 8,800 |
| Maybridge 2 | 704 |
| Maybridge 3 | 7,639 |
| Maybridge 4 | 4,576 |
| Maybridge 5 | 3,212 |
| Mixed Commercial Plate 1 | 352 |
| Mixed Commercial Plate 2 | 320 |
| Mixed Commercial Plate 3 | 251 |
| Mixed Commercial Plate 5 | 268 |
| NIBR 1 | 44,000 |
| Peakdale 1 | 2,816 |
| Peakdale 2 | 352 |

The screens may begin with known bioactive libraries, and then move on to less-well characterized libraries, for example, as listed in Table 3. The luciferase screen may be performed in duplicate in 384-well plates with an automated detection system optimized for HTS luciferase activity readout. Yeast strains harboring luciferase reporters driven by three Oaf1p binding sites, or three Gal4p UAS sites, have been generated, and hits from the screen can be counter-screened in these strains in the presence of oleic acid or galactose, respectively, to exclude general inhibitors of transcription, inhibitors of luciferase activity, and chemicals exhibiting cellular toxicity. The screen may yield a number of hits which may then be subjected to the counter screen(s), as well as several secondary assays, including inhibition of ketoconazole-dependent expression of CgCDR2 as assayed by qRT-PCR in C. glabrata, and increased sensitivity to azoles in C. glabrata MDR assays in vitro and in the C. elegans model as described (to validate the concept of co-therapeutics).

Lead compounds may inhibit azole-stimulated co-immunoprecipitation of CgPdr1p with CgGal11Ap and azole-induced association of CgPdr1p with the CgGal11Ap KIX domain. Whether lead compounds directly compete with radiolabeled ketoconazole in the cold competition assay, or whether they directly compete with binding of CgPdr1pAD to the CgGal11Ap KIX domain using NMR, may be determined. The most promising hits may then be subjected to medicinal chemistry, for example at the Partners Center for Drug Discovery (affiliated with MGH and providing at-cost medicinal chemistry), and iterative improvements using the assays described. If lead compounds bind to the CgPdr1p XBD or the CgGal11Ap KIX domain, NMR may then further characterize the binding sites for further structural refinements of compounds.

A potential challenge of the yeast high-throughput screen is the relative high concentrations of chemicals required to penetrate the yeast cell wall and to overcome the active drug efflux system to reach an intracellular concentration that effectively inhibits CgPdr1p xenobiotic-dependent gene activation to score in the luciferase assay. The chemical libraries can typically provide up to 10 µM concentration in the HTS assay, which may not be sufficient. The active compounds in the screen should actually decrease the expression of the drug efflux pumps, however, by inhibiting CgPdr1p. If the Gal4pDBD-CgPdr1pX-TAD fusion protein is capable of mediating xenobiotic response in human cells, a stable cell line with an integrated Gal4pDBD-CgPdr1pX-TAD expression cassette and a Gal4p UAS-luciferase reporter may be generated, and then screened with this cell line (mammalian cells are typically more penetrable to chemicals). A stable HEK293T cell line has been generated that has the integrated Gal4p UAS-luciferase reporter, and which responds to other Gal4p fusion proteins (e.g., Gal4p-VP16), hence this approach might be feasible. An alternative luciferase system that was developed with HTS assays in yeast in mind may also be adapted. McNabb et al., 4 Eukaryot Cell 1539-49 (2005).

Example 15

High-Throughput Screen for Small-Molecule Inhibitors of C. glabrata Pdr1p AD Interaction with the KIX Domain of the C. glabrata Gal11Ap Ortholog The identification of transcriptional co-activator targets for nuclear receptors have facilitated the development of novel drug screening assays that are based on the monitoring of ligand-dependent recruitment of co-activators. The present work has identified the Mediator and its Gal11p subunit as a co-activator required for Pdr1p/Pdr3p gene activation and whose recruitment might be specifically targeted by small-molecule inhibitors. A high-throughput screen for small-molecule inhibitors of C. glabrata Pdr1pAD interaction with C. glabrata Gal11Ap KIX domain employs a fluorescence anisotropy/polarization assay attaching a fluorescent chromophore (fluorescein or Oregon Green) to the N- or C-terminus of a shortened version of the activation domain following procedures described recently. Moerke et al., 128 Cell 257-67 (2007).

The Pdr1pAD of C. glabrata is 60% identical to S. cerevisiae but contains a 4-residue insertion. Fluorescence spectroscopy allows measurement of equilibrium dissociation constants for the CgPdr1pAD interaction with the CgGal11Ap KIX domain for different lengths of the AD. To select an optimal sequence for the fluorescence polarization assay a sub-micromolar KD, such as 100 nM, may be advantageous and the peptide might be as short as possible (<40 residues). Because the fluorescence chromophore should be immobilized upon interaction with the KIX domain, label should not be attached to a long flexible tail. NMR spectroscopy may be used to assign the resonances of bound AD and identify flexible regions with $^{15}$N-relaxation experiments. The results guide selection of an optimal binding segment. The assay can be validated with sure fluorescence anisotropy of the labeled peptide at increasing concentrations of C. glabrata Gal11Ap KIX domain, and a fit of the data will yield a KD for the labeled peptide. Next, whether the labeled peptide can be displaced with unlabeled peptide, and an $IC_{50}$ is measured. Only if the labeled peptide can be displaced may the assay be used. It also may be necessary to switch the label position. In general, procedures described previously in detail can be followed. Moerke et al., 2007; Roehrl et al., 43 Biochem. 16056-66 (2004); Roehrl et al., 101 P.N.A.S. 7554-59 (2004). This includes detailed protocols regarding the concentrations of labeled peptide and target protein to be used for given affinities. These initial conditions can be changed after the first screen to search for either fewer hits with higher affinities or more hits with weaker affinities. The screen may be performed with state-of-the-art robotic liquid handlers and plate readers.

This example high-throughput screen for small-molecule inhibitors of C. glabrata Pdr1p AD interaction with the KIX domain of the *C. glabrata* Gal11Ap ortholog employs AD peptides. For example, one Fluorescein-conjugated 15-amino acid AD peptide (FITC-LYNSLWGDLFSDVYL) (SEQ ID NO:13) was based on favorable NMR data using an unlabeled peptide. Subsequent affinity studies employing Fluorescence anisotropy revealed that this short Fluorescein-tagged(FTIC) CgPdr1pAD peptide has a low affinity (~210 µM) for the CgGal11Ap KIX domain (FIG. 8). This was consistent with the NMR studies where the small peptide shifted the dissociation kinetics to a fast exchange regime indicative of a weaker binding. An alternative, longer, 30-amino acid (FITC-LGTLDEFVNKGDLNELYNSLWGDLFSDVYL) (SEQ ID NO:14) Fluorescein-tagged activation domain peptide, CgPdr1pAD-30, and this peptide has a much higher affinity (~2 µM).

Because the sensitivity of the fluorescence polarization assay depends on the change in size upon binding, a GST-tagged-CgGal11Ap KIX domain was used, after ensuring that the Fluorescein-tagged CgPdr1pAD-30 peptide does not bind to GST. The conditions (salt and pH) were adjusted to obtain a binding constant that was in the high nanomolar range. The rationale was to have binding neither too tight (Kd<300 nM) or too weak (Kd>5 µM) with too little or too many hits, respectively. Optimal conditions had a binding constant of ~700 nM. The Z-score for the assay was 0.92, indicative of a good signal to noise in the screen.

For small molecule screening, Fluorescein-tagged CgPdr1pAD was held at a concentration of 30 nM and the GST-tagged-CgGal11Ap KIX domain was at a concentration of 1 µM (above the estimated Kd) The screen was done in duplicate in multiwall-plates, and the last two columns of each plate had 30 nM of CgPdr1pAD and 1 µM CgGal11Ap-KIX but did not have any compound added to it, thus serving as a negative control. The volume in each well was 30 µl. 100 nl of 5 mg/ml stock solution of the compound was added and the plates were incubated for 30 min before the samples were measured.

The following libraries of small molecules were screened in duplicate:

| Library name | Number of molecules |
|---|---|
| Biomol ICCB Known Bioactives3 | 430 |
| Ninds Custom Collection 2 | 1040 |
| Prestwick 1 Collection | 1120 |
| Asinex 1 | 12378 |
| ChemBridge 3 | 10560 |
| ChemDiv 4 | 14677 |
| Enamine 2 | 26576 |
| Life Chemicals 1 | 3893 |
| Maybridge 5 | 3212 |
| ChemDiv 3 | 16544 |
| Maybridge 1 | 8800 |
| ChemDiv 6 | 44000 |
| Total number of molecules | 143280 |

The Z-score for Fluorescence Polarization and Total Fluorescence was calculated individually for each plate. It is known fact that some small molecules in the screen are fluorescent themselves at the excitation and emission wavelengths of Fluorescein. This is referred to as "auto fluorescence" and will yield false positives in the assay. "Cherry picking" considered those compounds that have a Z-score of greater than 4 in fluorescence polarization and a Z-score of less than 3 in total fluorescence. The values were consistent in both samples (original and duplicate). From this list, 630 compounds were chosen after manually inspecting the compounds. Calculating the standard deviation of fluorescence polarization considered the readings from the entire plate, whereas for calculating the standard deviation of total fluorescence considered the last two columns. In order to have a strict filtering condition for the cherry picks, the mean and standard deviation for the total fluorescence from regions of plate without the compounds (i.e., last two columns) were calculated. This approach provides a strict measure to account for and discard false positives that arise from the auto fluorescence of the compounds (FIG. 9).

Compounds isolated form the screen may also target mammalian KIX domains. Secondary counter screens thus evaluate hits from the primary screens for ability to interact with the ARC105/MED15 and CBP KIX domains using NMR. Only lead compounds that specifically target CgGal11Ap KIX are pursued further. To address the potential issue of toxicity or undesirable side effects due to targeting of unrelated pathways in human cells, lead compounds to human cell lines can be added, and then DNA microarray analyses performed to assess whether the compounds affect other gene regulatory pathways in human cells. The results from these studies could then be cross-referenced with the recently developed chemical genomics database (e.g., Connectivity Map assembled by the Harvard/MIT Broad Institute) that is available for pathway identification. Lamb, 7 Nature Rev. 54-60 (2007).

Example 16

Evaluation of the Efficacy of Small Molecule Antagonists of Cg Pdr1p Xenobiotic-Dependent Gene Activation and Small Molecule Inhibitors of the CgPdr1-AD CgGal11-KIX Interaction in a High Throughput Cell Viability Screen Positive hits from the high throughput luciferase screen (example 14) or high-throughput screen for small-molecule inhibitors of the CgPdr1-AD CgGal11-KIX interaction (example 15) may be subjected to secondary screening in a high throughput viability assay. This assay is based on the rationale that hits from these screens will abrogate the upregulation of drug efflux pumps, thereby sensitizing yeast cells to low levels of xenobiotics, such as ketoconazole. This viability assay monitors the ability of these positive hits to reduce or eliminate yeast growth in the presence or absence of the ketoconazole, which serves as a representative of the azole class of antifungal compounds.

Briefly, *S. cerevisiae* or *C. glabrata* wild-type cells are grown to exponential growth phase and added to 384-well plates. Each well contains rich media with either (a) drug of interest or (b) drug of interest with ketoconazole. Serial 2-fold dilutions of compounds are tested to determine concentration-dependent effects upon cell viability. Cells are incubated at 30° C. and optical density ($OD_{600}$) is measured to determine cell growth. Plates are set up in duplicate and compounds are scored for their ability to inhibit cell growth in the presence or absence of ketoconazole.

For *S. cerevisiae* screening, wild-type inoculum cultures were grown in YPD (1% yeast extract, 2% bacto-peptone, 2% dextrose) at 30° C., 200 rpm overnight. On day 2, these cultures were expanded to log-phase growth in the morning ($OD_{600}$~0.500). On day 3, compounds of interest were added to 25 µL of YPD or YPD+10 µM ketoconazole at an initial concentration of 30 µg/mL and set up as 5 two-fold serial dilutions. Log-phase wild-type cultures with an $OD_{600}$~0.500 were diluted to an $OD_{600}$ of 0.005 and added at an equal volume (25 µL) of wild-type cells to wells with compounds +/− ketoconazole. Initial $OD_{600}$ values were read with a Perkin Elmer EnVision and plates incubated in a moist chamber at 30° C. $OD_{600}$ was read at 24 hr, 48 hr, 72 hr and 96 hr. Determination of which compounds inhibit cell growth can be done robotically. As positive controls, the allylamine derivative terbinafine was used to eliminate cell growth in the presence of ketoconazole. The Z-score for this assay was 0.84, indicative of a good signal to noise ratio for this screen.

To optimize C. glabrata screening, wild-type C. glabrata strains are grown in YPD or YPGE with increasing concentrations of ketoconazole to determine two concentrations at which a maximum difference in growth (as determined by $OD_{600}$) is achieved with a minimum change in concentration (from lower concentration X to higher concentration Y). Screening will be carried out in a manner similar to screening in S. cerevisiae; however, cells will be grown at concentration X (as determined in the optimization step) and concentration Y will be used as a positive control.

Figure 11:
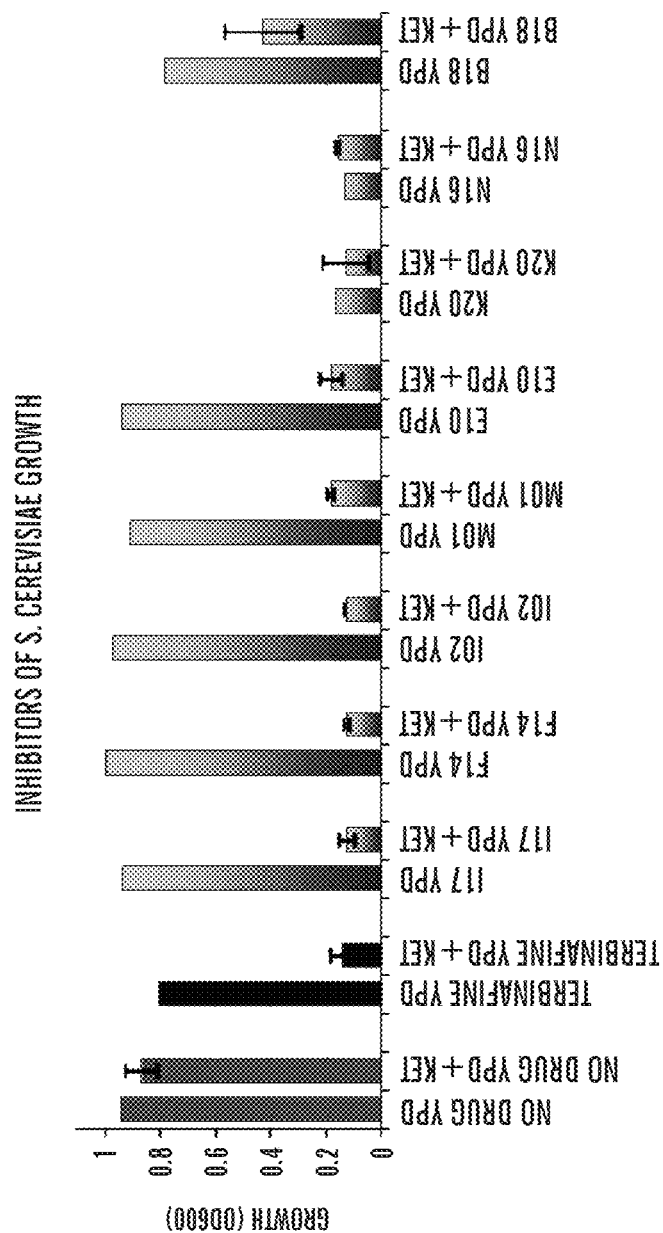
FIG. 11 is a bar graph depicting growth of S. cerevisiae in the presence of small-molecule inhibitors identified in a secondary viability screen in an embodiment of the present invention. Growth is indicated for cells in the presence of 30 µg/ml of the small molecule, in the absence or presence (+KET) of 5 µM ketoconazole.
Figure 12:
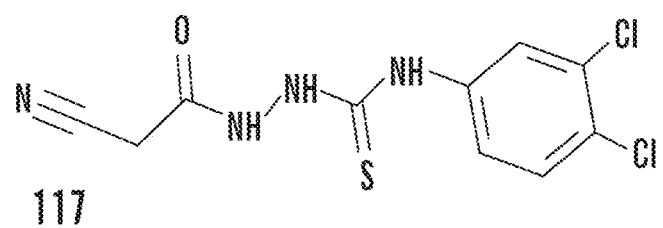
FIG. 12 shows the chemical structure of compound 117, a small-molecule inhibitor identified in a viability assay in an embodiment of the present invention.

Because the $OD_{600}$ assay provides us with a measure of growth, concentration-dependent effects on growth can be determined, as shown in FIG. 10. This assay identified compound N16 to be a concentration-dependent inhibitor of S. cerevisiae growth in the absence of ketoconazole; compounds E10 and B18 inhibit growth in the presence of ketoconazole but not alone. From the 350 small molecules initially screened in a secondary S. cerevisiae viability assay, eight small molecule inhibitors of growth were identified, five of which repress growth in the presence but not the absence of ketoconazole. The effect of these compounds on growth is shown in FIG. 11. A spot assay confirmed the sensitivity of wild-type S. cerevisiae cells to compounds K20 and I17 in the presence of ketoconazole. The structure of I17 is shown in FIG. 12.

Small molecules inhibitors identified in the viability assay can be further evaluated for their role in inhibiting fungal MDR by assessing drug sensitivity (example 6), transcription by quantitative real-time RT-PCR (example 4), inhibition of azole-induced protein association (example 14), fungal specificity (example 15) and potentiation of antifungal activity in a C. elegans model (example 17).

Example 17

Evaluation of the Efficacy of CgPdr1p Antagonists for Inhibition of Xenobiotic Gene Regulation and MDR in C. glabrata, and Potentiation of Antifungal Therapy in a C. elegans Model for Fungal Pathogenesis The antagonists/inhibitors identified, for example in Examples 14 and 15, may be further studied for their effects on the interaction of CgPdr1p with CgGal11Ap in vitro and in vivo, as well as for inhibition of xenobiotic-dependent trans-activation of CgPdr1p target genes and MDR in C. glabrata. They may also be examined for alleviation of MDR in the C. elegans model system to evaluate fungal pathogenicity and susceptibility to antifungals. This model is similar to the process of Candida infection in humans, insofar as Candida cells induce filament production, which is critical to infectivity in the human host. The C. elegans model also has a number of advantages over mammalian models, including rapid generation time, low cost, lack of ethical considerations, and simplicity of the assay, and represents a powerful tool for initial in vivo study of C. glabrata MDR and efficacy of small-molecule CgPdr1p inhibitors before going into experiments using more complex and expensive mouse models.

The antagonists/inhibitors may initially be tested for disruption of co-immunoprecipitation of full-length Myc-CgPdr1p with Flag-CgGal11Ap expressed in either S. cerevisiae or C. glabrata. Inhibition of the recruitment of the Mediator, as assessed by ChIP of Flag-CgGal11Ap in response to xenobiotics on the CgCDR1 and CgCDR2 promoters can be analyzed. Additionally, the effects of antagonists/inhibitors on xenobiotic-dependent activation of CgCDR1 and CgCDR2 expression in C. glabrata can be studied by qRT-PCR. Their efficacy in countering MDR by potentiation of the cytostatic action of antifungals, such as ketoconazole and fluconazole, in plate growth assay as well as in liquid culture, can be tested.

For the studies employing the C. elegans in vivo model, the proof-of-principle experiments showing that C. glabrata can infect C. elegans and kill most worms within six days was demonstrated (FIG. 4e) and C. glabrata are completely resistant to standard antifungal treatment with ketoconazole and fluconazole in the C. elegans model system. By contrast, C. glabrata harboring deletions of CgPDR1 or CgGAL11A are highly sensitive to antifungals in vitro, as well as in the C. elegans pathogenesis system (FIG. 4). See also Tsai et al., 50 Antimicrob. Agents Chemother. 1384-92 (2006); Vermitsky et al., 61 Mol. Microbiol. 704-22 (2006). These strains serve as positive controls when testing novel CgPdr1p antagonists/inhibitors for sensitization to different antifungals in C. elegans.

For these analyses, both wildtype (N2) C. elegans and nematodes harboring the glp-4;sek-1 double mutation that results in sterility at 25° C. consequently avoids problems with progeny production confounding the scoring of C. glabrata-dependent killing and which exhibits increased susceptibility to a range of pathogens. Breger et al., 3 PLoS Pathogens (2007). This strain was successfully employed to study the pathogenicity of Candida species and their sensitivity to antifungals. A liquid C. elegans-killing assay developed for antifungal sensitivity analysis will be used where worms are first infected on lawns of pathogenic C. glabrata grown on solid agar media, and then transferred to pathogen-free liquid media (see FIG. 4e). Percent survival of C. glabrata-infected worms is scored daily in the presence and absence of antifungals and CgPdr1p antagonists/inhibitors added to the liquid media at different concentrations. To examine toxicity of antagonists/inhibitors to worms, these compounds are added to worms initially grown on bacterial food (OP50) before transfer to liquid media and score survival rates. The effects of CgPdr1p antagonists/inhibitors are analyzed together with antifungal agents in reducing the fungal burden in the nematode intestine. In this assay, worms are collected after the various treatments and at different time points, washed, and then homogenized and plated on YPD agar containing bacterial antibiotics. Colony-forming units are then assessed.

It is anticipated that antagonists/inhibitors that antagonize CgPdr1p xenobiotic transactivation or directly disrupt CgPdr1pAD interaction with CgGal11Ap KIX will also impinge on the ability of CgPdr1p to interact with full-length CgGal11Ap, prevent recruitment of the Mediator (CgGal11Ap) to target genes in vivo, and interfere with xenobiotic-dependent transactivation of endogenous CgPdr1p-regulated genes. It is also expected that the antagonists/inhibitors will inhibit C. glabrata MDR in culture and in the C. elegans model. CgPdr1p antagonists/inhibitors from the initial screens might exhibit toxicity due to lack of specificity, or suffer from poor in vivo efficacy. Further structural and functional refinement could alleviate some of the problems.

The invention claimed is:

1. A method for the high throughput screening for agents that inhibit the multidrug resistance pathway in fungi comprising:

providing a solution of fluorescein-labeled Pdr1p activation domain, a Gal11p KIX domain and a test agent; and comparing the fluorescence polarization of the solution of fluorescein-labeled Pdr1p activation domain, the Gal11p KIX domain and the test agent, with the fluorescence polarization of a solution of fluorescein-labeled Pdr1p activation domain and a Gal11p KIX domain;

wherein the fluorescein-labeled Pdr1p activation domain consists of fluorescein and 30 amino acids of the CgPdr1p activation domain, having the amino acid sequence

LGTLDEFVNKGDLNELYNSLWGDLFSDVYL.

(SEQ ID NO: 14)

2. The method of claim 1, wherein the Gal11p-KIX domain is CgGal11Ap KIX.

3. The method of claim 1, wherein the Gal11p-KIX domain is GST-tagged.

4. The method of claim 1, wherein the comparing is automated.

* * * * *